United States Patent [19]
Perlin

[11] Patent Number: 6,068,977
[45] Date of Patent: *May 30, 2000

[54] METHOD AND SYSTEM FOR SEQUENCING GENOMES

[75] Inventor: Mark W. Perlin, Pittsburgh, Pa.

[73] Assignee: Cybergenetic Holdings, Inc., Pittsburgh, Pa.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/792,579

[22] Filed: Jan. 30, 1997

Related U.S. Application Data

[63] Continuation of application No. 08/504,400, Jul. 19, 1995, Pat. No. 5,604,100.

[51] Int. Cl.[7] .............................. C12Q 1/68; C12P 19/34; C12N 9/00; C07H 21/04
[52] U.S. Cl. ........................... 435/6; 435/91.1; 435/91.2; 435/183; 536/23.1; 536/24.3; 536/24.33
[58] Field of Search .................................. 435/5, 6, 91.1, 435/91.2, 183, 270, 287.2; 935/1, 8, 10, 76, 77; 436/94; 536/23.1, 24.3, 24.33

[56] References Cited

PUBLICATIONS

Sommer and Tautz, "Minimal homology requirements for PCR primers," Nucleic Acids Research, vol. 17, No. 16, p. 6749, 1989.

*Primary Examiner*—Kenneth R. Horlick
*Assistant Examiner*—Jeffrey Siew
*Attorney, Agent, or Firm*—Ansel M. Schwartz

[57] ABSTRACT

The present invention pertains to a method for sequencing genomes. The method comprises the steps of obtaining nucleic acid material from a genome. Then there is the step of constructing a clone library and one or more probe libraries from the nucleic acid material. Next there is the step of comparing the libraries to form comparisons. Then there is the step of combining the comparisons to construct a map of the clones relative to the genome. Next there is the step of determining the sequence of the genome by means of the map. The present invention also pertains to a system for sequencing a genome. The system comprises a mechanism for obtaining nucleic acid material from a genome. The system also comprises a mechanism for constructing a clone library and one or more probe libraries. The constructing mechanism is in communication with the nucleic acid material from a genome. Additionally, the system comprises a mechanism for comparing said libraries to form comparisons. The comparing mechanism is in communication with the said libraries. The system also comprises a mechanism for combining the comparisons to construct a map of the clones relative to the genome. The said combining mechanism is in communication with the comparisons. Further, the system comprises a mechanism for determining the sequence of the genome by means of said map. The said determining mechanism is in communication with said map. The present invention additionally pertains to a method for producing a gene of a genome.

19 Claims, 5 Drawing Sheets

METHOD AND SYSTEM FOR SEQUENCING GENOMES

This is a continuation of application Ser. No. 08/504,400 filed on Jul. 19, 1995, now U.S. Pat. No. 5,604,100.

FIELD OF THE INVENTION

The present invention pertains to a process for determining the DNA sequence of the genome of an organism. More specifically, the present invention is related to constructing clone maps of organisms, and then using these maps to direct the sequencing effort. The invention also pertains to systems that can effectively use this sequence and map information.

BACKGROUND OF THE INVENTION

A primary goal of the human genome project is to determine the entire DNA sequence for the genomes of human, model, and other useful organisms. A related goal is to construct ordered clone maps of DNA sequences at 100 kilobase (kb) resolution for these organisms (D. R. Cox, E. D. Green, E. S. Lander, D. Cohen, and R. M. Myers, "Assessing mapping progress in the Human Genome Project," *Science*, vol. 265, No. 5181, pp. 2031–2, 1994), incorporated by reference. Integrated maps that localize clones together with polymorphic genetic markers (J. Weber and P. May, "Abundant class of human DNA polymorphisms which can be typed using the polymerase chain reaction," *Am. J. Hum. Genet:.*, vol. 44, pp. 388–396, 1989), incorporated by reference, are particularly useful for positionally cloning human disease genes (F. Collins, "Positional cloning: lets not call it reverse anymore," *Nature Genet.*, vol. 1, No. 1, pp. 3–6, 1992), incorporated by reference. The greatest need, however, is for sequence-ready maps. Also useful are maps of expressed sequences. Human DNA sequences now exist as genomic libraries in a variety of small- and large-insert capacity cloning vectors, with yeast artificial chromosomes (YACs) (D. T. Burke, G. F. Carle, and M. V. Olson, "Cloning of large exogenous DNA into yeast by means of artificial chromosomes," *Science*, vol. 236, pp. 806–812, 1987), incorporated by reference, used extensively in mapping large regions. Efficient strategies for performing the requisite experimentation are critical for sequencing and mapping chromosomes or entire genomes.

The starting point for an effective sequencing method is a complete ordered clone map of a genome. Current strategies for ordering clones build contiguous sequences (contigs) using short-range comparison data. Sequence-tagged site (STS) (M. Olson, L. Hood, C. Cantor, and D. Botstein, "A common language for physical mapping of the human genome," *Science*, vol. 245, pp. 1434–35, 1989), incorporated by reference, comparisons with clones are used in STS-content mapping (SCM) (E. D. Green and P. Green, "Sequence-tagged site (STS) content mapping of human chromosomes: theoretical considerations and early experiences," *PCR Methods and Applications*, vol. 1, pp. 77–90, 1991), incorporated by reference. For chromosomal or genome-wide SCM, very large YACs (megaYACs) are required for the currently available STS densities (R. Arratia, E. S. Lander, S. Tavare, and M. S. Waterman, "Genomic mapping by anchoring random clones: a mathematical analysis," *Genomics*, vol. 11, pp. 806–827, 1991; W. J. Ewens, C. J. Bell, P. J. Donnelly, P. Dunn, E. Matallana, and J. R. Ecker, "Genome mapping with anchored clones: theoretical aspects," *Genomics*, vol. 11, pp. 799–805, 1991), incorporated by reference; these large YACs are often chimeric or contain gaps. Restriction fragment fingerprint mapping has been done with hybridization (C. Bellanne-Chantelot, B. Lacroix, P. Ougen, A. Billault, S. Beaufils, S. Bertrand, S. Georges, F. Glibert, I. Gros, G. Lucotte, L. Susini, J.-J. Codani, P. Gesnouin, S. Pook, G. Vaysseix, J. Lu-Kuo, T. Ried, D. Ward, I. Chumakov, D. Le Paslier, E. Barillot, and D. Cohen, "Mapping the whole genome by fingerprinting yeast artificial chromosomes," *Cell*, vol. 70, pp. 1059–1068, 1992; R. L. Stallings, D. C. Torney, C. E. Hildebrand, J. L. Longmire, L. L. Deaven, J. H. Jett, N. A. Doggett, and R. K. Moyzis, "Physical mapping of human chromosomes by repetitive sequence hybridization," *Proc. Natl. Acad. Sci. USA*, vol. 87, pp. 6218–6222, 1990), incorporated by reference, or without hybridization (A. Coulson, J. Sulston, S. Brenner, and J. Karn, "Toward a physical map of the genome of the nematode Caenorhabditis elegans," *Proc. Natl. Acad. Sci. USA*, vol. 83, pp. 7821–7825, 1986), incorporated by reference. With hybridization fingerprinting, path analysis of YAC fingerprints is not always reliable when constructing contigs. Hybridizing an internal clone sequence (e.g., end-clone sequence, Alu-PCR probes) against a library to determine neighboring sequences builds unpositioned YAC contigs (M. T. Ross and V. P. J. Stanton, "Screening large-insert libraries by hybridization," in *Current Protocols in Human Genetics*, vol. 1, N. J. Dracopoli, J. L. Haines, B. R. Korf, C. C. Morton, C. E. Seidman, J. G. Seidman, D. T. Moir, and D. Smith, ed. New York: John Wiley and Sons, 1995, pp. 5.6.1–5.6.34), incorporated by reference, although walking techniques are generally reserved for closing gaps.

The number of experiments needed for these short-range clone mapping approaches increases with the number of clones in the library. While considerable efficiency is gained by using multiplexed experiments with pooled reagents (G. A. Evans and K. A. Lewis, "Physical mapping of complex genomes by cosmid multiplex analysis," *Proc. Natl. Acad. Sci. USA*, vol. 86, No. 13, pp. 5030–4, 1989; E. D. Green and M. V. Olson, "Systematic screening of yeast artificial-chromosome libraries by use of the polymerase chain reaction," *Proc. Natl. Acad. Sci. USA*, vol. 87, No. 3, pp. 1213–7, 1990), incorporated by reference, the experimental requirements are at least proportional to the number of clones. A useful goal is to significantly reduce cost and increase throughput by achieving a number of required experiments largely independent of library size. One step toward this independence has been achieved by gridding an entire library onto nylon filters, and then hybridizing these filters with a set of probes (H. Lehrach, A. Drmanac, J. Hoheisel, Z. Larin, G. Lennon, A. P. onaco, D. Nizetic, G. Zehetner, and A. Poustka, "Hybridization fingerprinting in genome mapping and sequencing," in *Genetic and Physical Mapping I: Genome Analysis*, K. E. Davies and S. M. Tilghman, ed. Cold Spring Harbor, N.Y.: Cold Spring Harbor Laboratory, 1990, pp. 39–81; A. P. Monaco, V. M. S. Lam, G. Zehetner, G. G. Lennon, C. Douglas, D. Nizetic, P. N. Goodfellow, and H. Lehrach, "Mapping irradiation hybrids to cosmid and yeast artificial chromosome libraries by direct hybridization of Alu-PCR products," *Nucleic Acids Res.*, vol. 19, No. 12, pp. 3315–3318, 1991), incorporated by reference. For example, contigs of small genomic regions have been constructed by oligonucleotide fingerprinting of gridded cosmid filters (A. G. Craig, D. Nizetic, J. D. Hoheisel, G. Zehetner, and H. Lehrach, "Ordering of cosmid clones covering the herpes simplex virus type I," *Nucleic Acids Res.*, vol. 18, No. 9, pp. 2653–60, 1990; A. J. Cuticchia, J. Arnold, and W. E. Timberlake, "ODS: ordering DNA sequences, a physical mapping algorithm based on simulated annealing," *CABIOS*, vol. 9, No. 2, pp. 215–219, 1992), incorporated by reference.

To efficiently span larger genomic regions, radiation hybrid (RH) mapping (D. R. Cox, M. Burmeister, E. R. Price, S. Kim, and R. M. Myers, "Radiation hybrid mapping: a somatic cell genetic method for constructing high-resolution maps of mammalian chromosomes," *Science*, vol. 250, pp. 245–250, 1990), incorporated by reference, has been used to localize small DNA sequences (though not clones) into high-resolution bins. Relatively few PCR experiments with one 96-well plate library of RHs generally suffice for mapping STSs or genes to unique bins having 250 kb to 1 Mb average resolution. The very large multiple fragments in each RH clone efficiently cover much of a chromosome (or genome). Assaying a sequence for intersection against a set of RHs provides long-range relational information for localization much akin to somatic cell hybrid (SCH) mapping (M. C. Weiss and H. Green, "Human-mouse hybrid cell lines containing partial complements of human chromosomes and functioning human genes," *Proc. Natl. Acad. Sci. USA*, vol. 58, pp. 1104–1111, 1976), incorporated by reference. However, RH mapping offers much greater resolution than SCH or fluorescent in situ hybridization (FISH) mapping.

For highly optimized experimentation, it would be desirable to combine high-resolution long-range RH mapping with low-cost high-throughput filter hybridization techniques to map clones. One can serially probe a gridded clone library with a set of RHs (H. Lehrach, A. Drmanac, J. Hoheisel, Z. Larin, G. Lennon, A. P. Monaco, D. Nizetic, G. Zehetner, and A. Poustka, "Hybridization fingerprinting in genome mapping and sequencing," in *Genetic and Physical Mapping I: Genome Analysis*, K. E. Davies and S. M. Tilghman, ed. Cold Spring Harbor, N.Y.: Cold Spring Harbor Laboratory, 1990, pp. 39–81), in principle requiring a number of experiments that is independent of the clone library size and logarithmically related to the desired map resolution. However, complex hybridization probes such as RHs (or their Alu-PCR products) generate data containing considerable noise. This inherent uncertainty, together with the large clone insert size (which complicates conventional RH analysis), has thus far precluded high-resolution mapping of clones using RHs (J. Kumlien, T. Labella, G. Zehetner, R. Vatcheva, D. Nizetic, and H. Lehrach, "Efficient identification and regional positioning of YAC and cosmid clones to human chromosome 21 by radiation fusion hybrids," *Mammalian Genome*, vol. 5, No. 6, pp. 365–71, 1994), incorporated by reference.

Inner product mapping (IPM) is a hybridization-based method for achieving high-throughput, high-resolution RH mapping of clones (M. W. Perlin and A. Chakravarti, "Efficient construction of high-resolution physical maps from yeast artificial chromosomes using radiation hybrids: inner product mapping," *Genomics*, vol. 18, pp. 283–289, 1993), incorporated by reference, that overcomes this barrier. Experimental data have established that IPM is a highly rapid, inexpensive, accurate, and precise large-scale long-range mapping method, particularly when preexisting RH maps are available, and that IPM can replace or complement more conventional short-range mapping methods.

Improved mapping results can be obtained incrementally by gradually enlarging the data tables, a process which provides useful feedback to both experimentation and analysis. With additional RHs, the signal-to-noise characteristics of the clone profiles improve. This incremental process, and the relatively few RHs required for accurate mapping, follows the logarithmic number of the probes needed for IPM. For best mapping results, as many STS-typed RHs as feasible are used: with currently available high-throughput, robotically-assisted hybridization methods, the localization benefits of performing many filter hybridizations outweigh the relatively low experimentation costs. The incremental construction also highlights IPM's indirect inference of map location: STS-content mapping directly compares clones with STSs, and can not map small-insert clones against STSs which are insufficiently dense.

IPM builds accurate maps from low-confidence data. IPM's partitioning of the experiments into two data tables of (A) clones vs. RHs and (B) RHs vs. STSs also partitions the data noise. Table B is formed from relatively noiseless PCR-based comparisons of STSs against RH DNA, and can thus accurately order and position the STS bins using combinatorial mapping procedures (M. Boehnke, "Radiation hybrid mapping by minimization of the number of obligate chromosome breaks," *Genetic Analysis Workshop 7: Issues in Gene Mapping and the Detection of Major Genes. Cytogenet Cell Genet*, vol. 59, pp. 96–98, 1992; M. Boehnke, K. Lange, and D. R. Cox, "Statistical methods for multipoint radiation hybrid mapping," Am. J. Hum. Genet., vol. 49, pp. 1174–1188, 1991), incorporated by reference. Table A is formed from inherently unreliable and inconsistently replicated hybridizations of complex RH probes against gridded filters. Inner product mapping uses the table B data matrix to ameliorate these data errors and robustly translate a clones's noisy RH signature vector (a row of table A) into a chromosomal profile, whose peak bins the clone.

IPM is a proven approach for mapping YACs (C. W. Richard III, D. J. Duggan, K. Davis, J. E. Farr, M. J. Higgins, S. Qin, L. Zhang, T. B. Shows, M. R. James, and M. W. Perlin, "Rapid construction of physical maps using inner product mapping: YAC coverage of chromosome 11," in *Fourth Internat'l Conference on Human Chromosome* 11, September 22–24, Oxford, England, 1994), incorporated by reference, and is a candidate method for mapping PACs (P. A. Ioannou, C. T. Amemiya, J. Garnes, P. M. Kroisel, H. Shizuya, C. Chen, M. A. Batzer, and P. J. de Jong, "UA new bacteriophage P1-derived vector for the propagation of large human DNA fragments," *Nature Genet.*, vol. 6, No. 1, pp. 84–89, 1994), incorporated by reference, cosmids, expressed sequences (M. D. Adams, J. M. Kelley, J. D. Gocayne, M. Dubnick, M. H. Polymeropoulos, H. Xiao, C. R. Merril, A. Wu, B. Olde, R. F. Moreno, A. R. Kerlavage, W. R. McCombie, and J. C. Venter, "Complementary DNA sequencing: Expressed sequence tags and human genome project," *Science*, vol. 252, pp. 1651–1656, 1991), incorporated by reference, and other physical reagents (J. D. McPherson, C. Wagner-McPherson, M. Perlin, and J. J. Wasmuth, "A physical map of human chromosome 5 (Abstract)," *Amer. J. Hum. Genet.*, vol. 55, No. 3 Supplement, pp. A265, 1994), incorporated by reference. Hybridization efficiency for table A can be improved by using long and IRE-bubble PCR (D. J. Munroe, M. Haas, E. Bric, T. Whitton, H. Aburatani, K. Hunter, D. Ward, and D. E. Housman, "IRE-bubble PCR: a rapid method for efficient and representative amplification of human genomic DNA sequences from complex sources," *Genomics*, vol. 19, No. 3, pp. 506–14, 1994), incorporated by reference, to reduce false negative errors, providing controls and redundant DNA spotting for internal calibration, and directly acquiring signals (e.g., via a phosphorimager, Molecular Dynamics, Sunnyvale, Calif.) to facilitate automated scoring. Current robotic technologies enable the high-throughput construction of gridded filters (A. Copeland and G. Lennon, "Rapid arrayed filter production using the 'ORCA' robot," *Nature*, vol. 369, No. 6479, pp. 421–422, 1994), incorporated by reference; single use of these filters would reduce the time and error related to stripping and reprobing. Robots similarly provide high-throughput PCR comparisons for constructing table B. Alternatively, existing RH mapping data can be rapidly extended (at low cost) into inner product maps of libraries (U. Francke, E. Chang, K. Comeau, E.-M. Geigl, J. Giacalone, X. Li, J. Luna, A. Moon, S. Welch, and P. Wilgenbus, "A radiation hybrid map of human chromosome 18," *Cytogenet. Cell Genet.*, vol. 66, pp. 196–213, 1994), incorporated by reference.

Whole human genome RH (WG-RH) libraries of 0.5 and 1.0 Mb resolution have been constructed (D. R. Cox, K. O'Connor, S. Hebert, M. Harris, R. Lee, B. Stewart, G. DiSibio, M. Boehnke, K. Lange, R. Goold, and R. M. Myers, "Construction and analysis of a panel of "whole genome" radiation hybrids (Abstract)," *Amer. J. Hum. Genet.*, vol. 55, No. 3 Supplement, pp. A23, 1994; M. A. Walter, D. J. Spillett, P. Thomas, J. Weissenbach, and P. N. Goodfellow, "A method for constructing radiation hybrid maps of whole genomes," *Nature Genet.*, vol. 7, No. 1, pp. 22–28, 1994), incorporated by reference, and have been characterized for the STSs used in the genome-wide CEPH megaYAC STS-content map (T. Hudson, S. Foote, S. Gerety, J. Ma, S.-h. Xu, X. Hu, J. Bae, J. Silva, J. Valle, S. Maitra, A. Colbert, L. Horton, M. Anderson, M. P. Reeve, M. Daly, A. Kaufman, C. Rosenberg, L. Stein, N. Goodman, J. Orlin, D. C. Page, and E. S. Lander, "Towards an STS-content map of the human genome (Abstract)," *Amer. J. Hum. Genet.*, vol. 55, No. 3 Supplement, pp. A23, 1994), incorporated by reference. The availability of this WG-RH table B resource suggests that constructing table A by performing hybridizations between species specific (e.g., Alu-PCR) products of these RHs and gridded clones or expressed sequences, and then combining tables A and B to build a genome-wide inner product map, is a fast, accurate, and inexpensive approach to whole genome physical mapping. IPM has localized the components of chimeric YACs as distinct multiple peaks. IPM is therefore useful in verifying and extending current megaYAC mapping projects, and in multiplexed experimental designs that pool sequences from well-separated bins.

IPM provides long-range mapping information for DNA sequences relative to RH bins through DNA hybridization. This binning information can be complemented with short-range mapping data, such as oligonucleotide fingerprint hybridizations (H. Lehrach, A. Drmanac, J. Hoheisel, Z. Larin, G. Lennon, A. P. Monaco, D. Nizetic, G. Zehetner, and A. Poustka, "Hybridization fingerprinting in genome mapping and sequencing," in *Genetic and Physical Mapping I: Genome Analysis*, K. E. Davies and S. M. Tilghman, ed. Cold Spring Harbor, N.Y.: Cold Spring Harbor Laboratory, 1990, pp. 39–81), incorporated by reference, and (R. Drmanac, Z. Strezoska, I. Labat, S. Drmanac, and R. Crkvenjakov, "Reliable hybridization of oligonucleotides as short as six nucleotides," *DNA Cell Biol.*, vol. 9, No. 7, pp. 527–534, 1990), incorporated by reference. Combining the data from these two high-throughput hybridization studies enables a two-pass BIN-SORT (A. V. Aho, J. E. Hopcroft, and J. D. Ullman, *Data Structures and Algorithms*. Reading, Mass.: Addison-Wesley, 1983), incorporated by reference, strategy to high-resolution mapping: first use IPM to bin the clones, and then use short-range data to determine the orders and distances of clone subsets in proximate bins. This strategy can rapidly construct minimum-length paths of sequence-ready clones that tile the genome. Crucially, such IPM-derived contigs overcome the short-range limitations of all other known mapping methods, and enable the coordinated sequencing of the human genome, which is a well-recognized goal (F. Collins and D. Galas, "A new five-year plan for the U.S. Human Genome Project," *Science*, vol. 262, pp. 43–46, 1993), incorporated by reference. Such combination approaches can be highly effective for other purposes, such as using short-range proximity data to sharpen long-range inner product map results. IPM's experimental efficiencies enable effective determination of genome-wide DNA sequences, and the construction of high-resolution integrated genome maps for human, model organism, and agricultural species.

This invention pertains to determining the sequence of the genome of an organism or species through the use of a novel, unobvious, and highly effective clone mapping strategy. Such sequence information can be used for finding genes of known utility, determining structure/function properties of genes and their products, elucidating metabolic networks, understanding the growth and development of humans and other organisms, and making comparisons of genetic information between species. From these studies, diagnostic tests and pharmacological agents can be developed of great utility for preventing and treating human and other disease.

SUMMARY OF THE INVENTION

The present invention pertains to a method for sequencing genomes. The method comprises the steps of obtaining nucleic acid material from a genome. Then there is the step of constructing a clone library and one or more probe libraries from the nucleic acid material. Next there is the step of comparing the libraries to form comparisons. Then there is the step of combining the comparisons to construct a map of the clones relative to the genome. Next there is the step of determining the sequence of the genome by means of the map.

The present invention also pertains to a system for sequencing a genome. The system comprises a mechanism for obtaining nucleic acid material from a genome. The system also comprises a mechanism for constructing a clone library and one or more probe libraries. The constructing mechanism is in communication with the nucleic acid material from a genome. Additionally, the system comprises a mechanism for comparing said libraries to form comparisons. The comparing mechanism is in communication with the said libraries. The system also comprises a mechanism for combining the comparisons to construct a map of the clones relative to the genome. The said combining mechanism is in communication with the comparisons. Further, the system comprises a mechanism for determining the sequence of the genome by means of said map. The said determining mechanism is in communication with said map.

The present invention additionally pertains to a method for producing a gene of a genome. The method comprises the steps of obtaining nucleic acid material from a genome. Then there is the step of constructing libraries from the nucleic acid material. Next there is the step of comparing the libraries to form comparisons. Then there is the step of combining the comparisons to construct a map of the clones relative to the genome. Next there is the step of localizing a gene on the map. Then there is the step of cloning the gene from the map.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

A genome is any portion of the inherited nucleic acid material, or its derivatives, of one or more individuals of any species. In particular, it comprises the DNA sequences that are to be determined or mapped.

A clone is a DNA sequence having insert size between 50 bp and 5 Mb that is part of a genome.

A clone library is a set of clones, preferrably of like insert sizes.

Two DNA sequences are said to overlap when they share common subsequences, and this commonality can be detected by an experiment, including polymerase chain reaction (PCR) or DNA hybridization.

A contig is a set of overlapping clones.

A probe is a preparation of one or more DNA sequences that is suitable for overlap comparisons with other DNA sequences.

A long-range probe (relative to a clone library) is a DNA sequence having size preferrably greater than or equal to one half the average insert size of a clone library that is part of a genome.

A multiplexed long-range probe (relative to a clone library) is a single probe comprised of one or more long-range probes (relative to a clone library).

A long-range probe library (relative to a clone library) is a set of long-range probes (relative to a clone library), which are preferrably multiplexed.

A short-range probe (relative to a clone library) is a DNA sequence which examines a region of a genome preferrably less than or equal to twice the average insert size of a clone library that is part of said genome.

A multiplexed short-range probe (relative to a clone library) is a single short-range probe (relative to a clone library) which examines one or more regions of a genome.

A short-range probe library (relative to a clone library) is a set of short-range probes (relative to a clone library), which are preferrably multiplexed.

A bin probe is a DNA sequence that is part of a genome and that can be used to position DNA sequences relative to the genome.

A bin probe library is a set of bin probes.

(1) A Method and System for Determining the Sequence of Genomes

Figure 1:
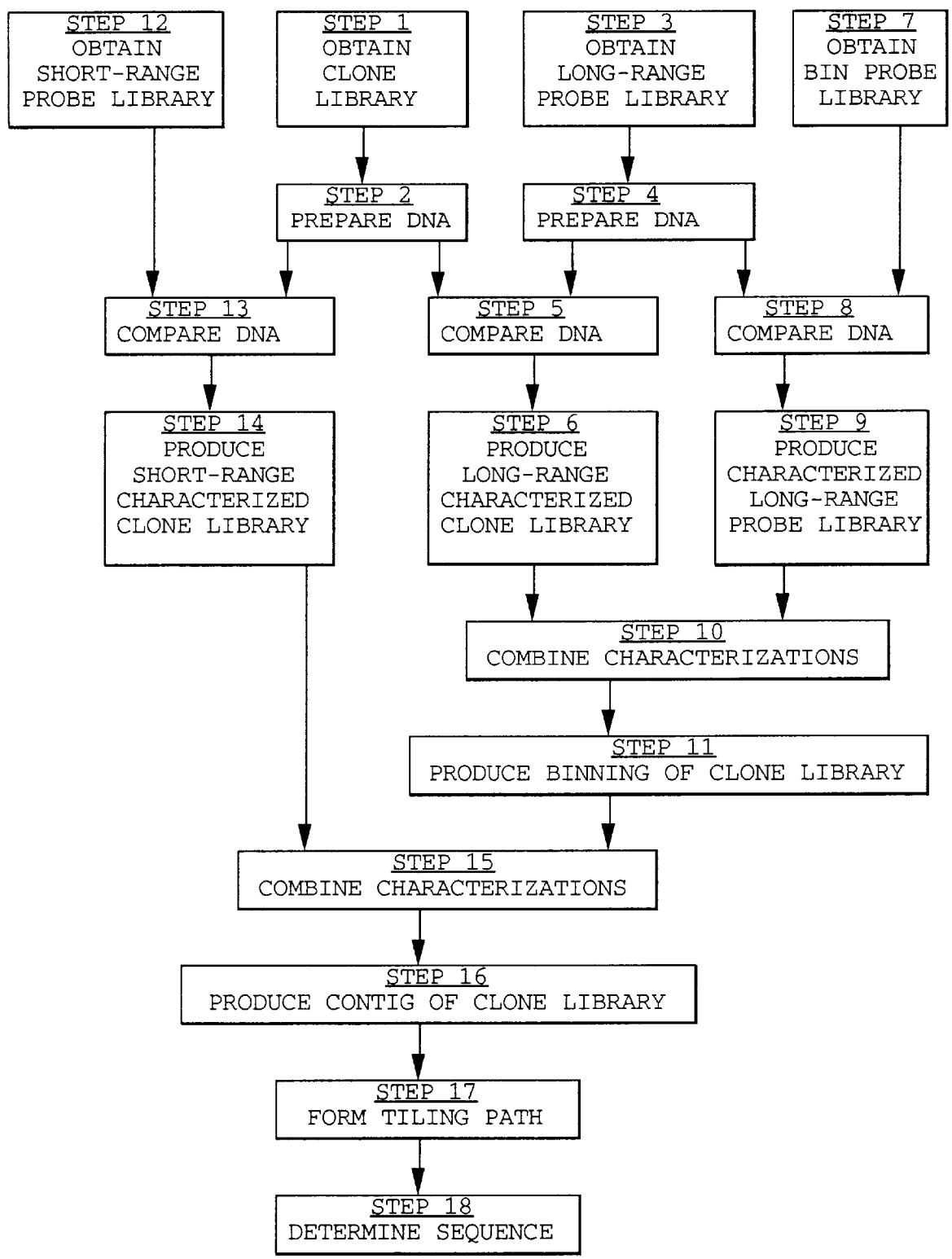
FIG. 1 is a flow chart of a method for sequencing genomes.

Referring to FIG. 1, a method is described for sequencing genomes that is comprised of the steps:

(1) Obtaining a clone library to be sequenced and mapped;

(2) Preparing DNA from individual clones in the clone library for comparison experiments;

(3) Obtaining a long-range probe library relative to the clone library;

(4) Preparing DNA from members of the long-range probe library for comparison experiments;

(5) Comparing DNA from the clone library with DNA from the long-range probe library;

(6) Producing a clone library characterized by long-range probes;

(7) Obtaining a bin probe library suitable for positioning the DNA sequences of long-range probes relative to the genome;

(8) Comparing DNA from the bin probe library with DNA from the long-range probe library;

(9) Producing a long-range probe library whose DNA sequences have been characterized by binning information relative to the genome;

(10) Combining the clone vs. long-range probe characterization from step 6, together with the long-range probe vs. genome binning characterization from step 9;

(11) Producing a binning of the clone library;

(12) Obtaining a short-range probe library relative to the clone library;

(13) Comparing DNA from the clone library with DNA from the short-range probe library;

(14) Producing a clone library characterized by short-range probes;

(15) Combining the long-range binning of the clone library from step 11, together with the short-range probing of the clone library from step 14;

(16) Producing a contig of the clone library which bins and orders clones relative to the genome;

(17) Forming a tiling path of clones that span genome regions;

(18) Determining the sequence of said clones, and of the entire genome.

Referring to FIG. 1, step 1 is for obtaining a clone library to be sequenced and mapped.

The clones may be comprised of large-sized clones that have genomic inserts greater than 250 kb (e.g., YACs), medium-sized clones that have genomic inserts greater than 50 kb, but less than 250 kb (e.g., PACs, BACs, P1s, or YACs), or small-sized clones that have genomic inserts less than 50 kb (e.g., cosmids, plasmids, phage, phagemids, or cDNAs). In the preferred embodiment, the clone library has at least two-fold redundancy relative to the genome. The technology for constructing these clones is well described (F. M. Ausubel, R. Brent, R. E. Kingston, D. D. Moore, J. G. Seidman, J. A. Smith, and K. Struhl, ed., Current Protocols in Molecular Biology. New York, N.Y.: John Wiley and Sons, 1995; N. J. Dracopoli, J. L. Haines, B. R. Korf, C. C. Morton, C. E. Seidman, J. G. Seidman, D. T. Moir, and D. Smith, ed., Current Protocols in Human Genetics. New York: John Wiley and Sons, 1995; J. Sambrook, E. F. Fritsch, and T. Maniatis, Molecular Cloning, Second Edition. Plainview, N.Y.: Cold Spring Harbor Press, 1989), incorporated by reference. Chromosome-specific cosmid clones are available from Los Alamos National Laboratories (Los Alamos, N.Mex.), genome-wide PAC clones from Pieter de Jong (Roswell Park, Buffalo, N.Y.), and the Genethon YAC libraries from the national genome center GESTECs, including the Whitehead Institute (Cambridge, Mass.). Libraries are also provided by commercial vendors, including cDNA libraries (ATCC, Rockville, Md.), P1 libraries (DuPont/Merck Pharmaceuticals, Glenolden, Pa.), BAC libraries (Research Genetics, Huntsville, Ala.), and cDNAs and other genome-wide resources (BIOS Labs, New Haven, Conn.).

Referring to FIG. 1, step 2 is for preparing DNA from individual clones in the clone library for comparison experiments.

In the preferred embodiment, DNA from the clones is prepared for DNA hybridization experiments. For DNA derived from bacterial clones (cosmids, PACs, etc.), two straightforward protocols are: (a) growing up colonies for each clone, and then lysing the bacterial cells to expose the cloned insert DNA, or (b) specifically extracting the DNA material from the clone using DNA prep such as an ion exchange column (Qiagen, Chatsworth, Calif.). When using vectors with more complex genomes (e.g., yeast cells), a species-specific DNA prep (e.g., Alu-PCR or IRE-bubble PCR) is preferred. This DNA from each clone is then gridded onto nylon membranes such as Hybond N+ (Amersham, Arlington Heights, Ill.) to prepare for subsequent DNA hybridization experiments (Hybond N+ product protocol, ver. 2), incorporated by reference.

Referring to FIG. 1, step 3 is for obtaining a long-range probe library relative to the clone library.

The preferred long-range multiplexed probe is the radiation hybrid (RH) (D. R. Cox, M. Burmeister, E. R. Price, S. Kim, and R. M. Myers, "Radiation hybrid mapping: a somatic cell genetic method for constructing high-resolution maps of mammalian chromosomes," *Science*, vol. 250, pp. 245–250, 1990; S. J. Goss and H. Harris, "New method for mapping genes in human chromosomes," *Nature*, vol. 255, pp. 680–684, 1975; S. J. Goss and H. Harris, "Gene transfer by means of cell fusion: statistical mapping of the human X-chromosome by analysis of radiation-induced gene segregation," *J. Cell. Sci.*, vol. 25, pp. 17–37, 1977), incorporated by reference. Chromosome-specific RH libraries have been constructed for other human chromosomes (M. R. James, C. W. Richard III, J.-J. Schott, C. Yousry, K. Clark, J. Bell, J. Hazan, C. Dubay, A. Vignal, M. Agrapart, T. Imai, Y. Nakamura, M. Polymeropoulos, J. Weissenbach, D. R. Cox, and G. M. Lathrop, "A radiation hybrid map of 506 STS markers spanning human chromosome 11," *Nature Genetics*, vol. 8, No. 1, pp. 70–76, 1994; S. H. Shaw, J. E. W. Farr, B. A. Thiel, T. C. Matise, J. Weissenbach, A. Chakravarti, and C. W. Richard, "A radiation hybrid map of 95 STSs spanning human chromosome 13q," *Genomics*, vol. 27, No. 3, pp. 502–510, 1995; U. Francke, E. Chang, K. Comeau, E.-M. Geigl, J. Giacalone, X. Li, J. Luna, A. Moon, S. Welch, and P. Wilgenbus, "A radiation hybrid map of human chromosome 18," *Cytogenet. Cell Genet.*, vol. 66, pp. 196–213, 1994), incorporated by reference. Whole-genome RHs (WG-RHs) for humans and other mammalian genomes have also been developed (M. A. Walter, D. J. Spillett, P. Thomas, J. Weissenbach, and P. N. Goodfellow, "A method for constructing radiation hybrid maps of whole genomes," *Nature Genet.*, vol. 7, no. 1, pp. 22–28, 1994), incorporated by reference, including the high-energy Stanford set (David Cox, Stanford, Calif.) and the low-energy Genethon set; the DNAs from both WG-RH sets are available (Research Genetics, Huntsville, Ala.).

There are alternative embodiments that can construct long-range multiplexed probes. One alternative embodiment is the use of rare cutter restriction enzymes (e.g., Not1 partial digests) to develop large DNA sequences from genomes. These fragments can be purified using pulsed-field gel electrophoresis (D. C. Schwartz and C. R. Cantor, "Separation of yeast chromosome-sized DNAs by pulsed field gradient gel electrophoresis," *Cell*, vol. 37, pp. 67–75, 1984), incorporated by reference, and then selectively pooled. A second alternative embodiment is the use of a second clone library that has a larger average insert size than the first clone library in step 1. Subsets of these larger insert clones can be pooled together to form a long-range probe library (relative to the first clone library). A third alternative embodiment which is particularly useful in animal models is the use of genetically inbred strains. with an F1 backcross between strains A and B, the meiotic events produce an interleaving of large chromosomal fragments of strains A and B. A subtractive hybridization can selectively remove the DNA from strain B, leaving behind just the large chromosomal regions of strain A for each F1 individual. This procedure constructs a long-range probe library (relative to the strain A clone library). The subtractive hybridization can be performed by first digesting the F1 individual genome with restriction enzymes, and then using whole genome DNA from strain B bound to solid support to selectively remove the strain B DNA.

Referring to FIG. 1, step 4 is for preparing DNA from members of the long-range probe library for comparison experiments.

The long-range probe DNA often resides in a complex background genome. In the RH embodiment, the background is murine genome, while in the pooled YAC embodiment, the background is the yeast genome. Therefore, the DNA preparations for these long-range probe embodiments preferably use a species-specific DNA extraction and amplification. The particular assay often depends on the clone library used.

When the clonal inserts reside in a complex background genome, such as YACS, inter-Alu hybridization is the preferred approach in step 5. In this case, Alu-PCR preparation of the long-range probes (M. T. Ross and V. P. J. Stanton, "Screening large-insert libraries by hybridization," in *Current Protocols in Human Genetics*, vol. 1, N. J. Dracopoli, J. L. Haines, B. R. Korf, C. C. Morton, C. E. Seidman, J. G. Seidman, D. T. Moir, and D. Smith, ed. New York: John Wiley and Sons, 1995, pp. 5.6.1–5.6.34), incorporated by reference, is the preferred embodiment. An alternative embodiment when background hybridization noise may be greater is IRE-bubble PCR (D. J. Munroe, M. Haas, E. Bric, T. Whitton, H. Aburatani, K. Hunter, D. Ward, and D. E. Housman, "IRE-bubble PCR: a rapid method for efficient and representative amplification of human genomic DNA sequences from complex sources," *Genomics*, vol. 19, No. 3, pp. 506–14, 1994), incorporated by reference.

When the clonal inserts are sufficiently large to contain inter-Alu regions, and the vector genome is not complex (e.g., bacterial), then IRE-bubble PCR is the preferred embodiment. This situation applies to many clone libraries, including cosmids, PACs, BACs, and P1s.

When the clonal inserts are too small to contain inter-Alu subsequences detectable by hybridization (such as cDNAs), an assay that provides for more uniform DNA expression from the long-range probes may be needed. The most preferred embodiment is then to use a multiplicity of restriction enzyme digests, each followed by long PCR between Alu repeats, and to then pool the PCR products to construct a probe. A second approach is a variation on direct selection (M. Lovett, J. Kere, and L. M. Hinton, "Direct selection: a method for the isolation of cDNAs encoded by large genomic regions," *Proc. Natl. Acad. Sci. U.S.A.*, vol. 88, pp. 9628–9632, 1991), incorporated by reference. In this approach, Lovett's cDNAs are replaced by a full restriction digest with a frequent-cutter of the long-range probe DNA, and Lovett's genomic contig is replaced with repetitive DNA (e.g., Alu or Cot-1) that selects for the same genome as the species-specific long-range probe. The result is a PCR amplification (via the end priming sites) of the long-range probe that is species specific (via the Alu selection).

The species-specific DNA is then amplified and labeled for use as a hybridization probe. In the preferred embodiment, this amplification and labeling is performed using a labeled dNTP with the random primer method (A. P. Feinberg and B. Vogelstein, "A technique for radiolabeling DNA restriction endonuclease fragments to high specific activity," *Analyt. Biochem.*, vol. 132, pp. 6–13, 1983; N. J. Dracopoli, J. L. Haines, B. R. Korf, C. C. Morton, C. E. Seidman, J. G. Seidman, D. T. Moir, and D. Smith, ed., *Current Protocols in Human Genetics*. New York: John Wiley and Sons, 1995), incorporated by reference. In one embodiment, $^{32}$P-dNTP is incorporated into a random primer PCR amplification, possibly using a kit such as the DECprime II DNA labeling kit (Ambion, Austin, Tex.). Other isotopes such as $^{35}$S or $^{33}$P can be used. In alternative embodiments, nonisotopic labeling is performed (L. J. Kricka, ed., *Nonisotopic Probing, Blotting, and Sequencing, Second Edition*. San Diego, Calif.: Academic Press, 1995), incorporated by reference.

Referring to FIG. 1, step 5 is for comparing DNA from the clone library with DNA from the long-range probe library.

The labeled long-range probe DNA is hybridized against the gridded clone library (A. P. Monaco, V. M. S. Lam, G. Zehetner, G. G. Lennon, C. Douglas, D. Nizetic, P. N. Goodfellow, and H. Lehrach, "Mapping irradiation hybrids to cosmid and yeast artificial chromosome libraries by direct hybridization of Alu-PCR products," *Nucleic Acids Res.*, vol. 19, No. 12, pp. 3315–3318, 1991), incorporated by reference. In an alterative embodiment, the roles of the long-range probe library and the clone library are reversed, with the long-range probe immobilized on the membrane and the label on the clone.

The hybridization comparison is done by preannealing the probe with 25 ng of Cot-1 DNA (Gibco-BRL, Grand Island, N.Y.) for 2 hours at 37° C. before adding to the prehybridization mix. The nylon filters containing the spotted clone DNA is then prehybridized overnight per manufacturer's instructions (Amersham, Arlingon Heights, Ill.), except for the addition of sheared, denatured human placental DNA at a final concentration of 50 ng/ml. Filters are hybridized overnight at 68° C., washed three times with final wash of 0.1 SSPE/0.1% SDS at 72° C., before exposing to autoradiographic film for 1 to 8 days. The exposed film image is then electronically scanned into a computer with memory. A phosphorimager (Molecular Dynamics, Sunnyvale, Calif.) or other electronic device can be used for imaging without the use of film.

For every RH hybridization probing, each of the clone positions on the autoradiographs of the gridded filters are scored on a numerical scale, such as 1–5, with 1 negative, 2 equivocal, 3 weakly positive, 4 positive, and 5 strongly positive. When duplicate typings are available, the maximum of the two scores is used, since there is a very high false-negative rate in the hybridization data. This data entry can be facilitated by use of an interactive computer program that presents the electronic image of the filter on a computer display, or by automated computer interpretation of the scanned image.

Referring to FIG. 1, step 6 is for producing a clone library characterized by long-range probes.

The hybridization experiments of step 5 construct a table of scores that compare the DNA from clones against DNA from long-range probes for detectable sequence similarity, and thus presumed genomic colocalization. The scores are rescaled so that the new scaling is approximately linear (C. C. Clogg and E. S. Shihadeh, *Statistical Models for Ordinal Variables*. Thousand Oaks, Calif.: Sage Press, 1994), incorporated by reference. That is, a unit increase in the scaling indicates a unit increase in the confidence one holds that the clone actually hybridized with the long-range probe. An equivocal event is scored as a 0, since it was equally likely to be negative or positive. A negative event is scored as –1, since there is high confidence that no observable hybridization has occurred; both positive and strongly positive events are scored as 1, since there is certainty that a hybridization event has occurred. A weakly positive event can be scored at 0.67 when a single typing is available, since there is considerably more confidence that it is positive than negative, and is considered equivocal when duplicate typings were available. For any scale used, the data is scored in a manner determined by the laboratory investigator and data analyst. This rescaled clone vs. probe comparison table A is stored in the memory of a computational device.

With perfectly clean comparison data (i.e., very low false negative and false positive rates), this table A might suffice for ordering the clones using conventional RH mapping methods. However, the high-throughput hybridization experiments incur a large noise cost. Therefore, some correction data is required to accurately map the clones. This correction stage is performed in the following steps 7–11.

Referring to FIG. 1, step 7 is for obtaining a bin probe library suitable for positioning the DNA sequences of long-range probes relative to the genome.

In the preferred embodiment, the bin probe library is comprised of sequence-tagged sites (STSs). For positional cloning applications, many of the STSs are preferably made polymorphic. The genetic or physical markers to be used for each STS are obtained as PCR primer sequences pairs and PCR reaction conditions from available Internet databases (Genbank, Bethseda, Md.; GDB, Baltimore, Md.; EMBL, Cambridge, UK; Genethon, Ervy, France; Stanford Genome Center, Stanford, Calif; Whitehead Institute Genome Center, Cambridge, Mass.; G. Gyapay, J. Morissette, A. Vignal, C. Dib, C. Fizames, P. Millasseau, S. Marc, G. Bernardi, M. Lathrop, and J. Weissenbach, "The 1993–94 Genethon Human Genetic Linkage Map," *Nature Genetics*, vol. 7, No. 2, pp. 246–339, 1994; Hilliard, Davison, Doolittle, and Roderick, Jackson laboratory mouse genome database, Bar Harbor, Me.; MapPairs, Research Genetics, Huntsville, Ala.), incorporated by reference. Alternatively, STSs can be constructed using existing techniques (Sambrook, J., Fritsch, E.F., and Maniatis, T. 1989. *Molecular Cloning, second edition*. Plainview, N.Y.: Cold Spring Harbor Press; N. J. Dracopoli, J. L. Haines, B. R. Korf, C. C. Morton, C. E. Seidman, J. G. Seidman, D. T. Moir, and D. Smith, ed., *Current Protocols in Human Genetics*. New York: John Wiley and Sons, 1995), incorporated by reference.

In a first alternative embodiment, the locations of the long-range probe fragments are localized on the genome by fluorescence in situ hybridization (FISH) studies. In these FISH studies, the nuclear DNA of the genome serves as the bin probe. In a second alternative embodiment, the binning is effected by comparison with previously positioned DNA probes, including mapped clone libraries, ESTs, or PCR primers.

Referring to FIG. 1, step 8 is for comparing DNA from the bin probe library with DNA from the long-range probe library.

In the preferred embodiment, PCR amplifications are carried out between the STSs in the bin probe library and the RH (or other) DNAs in the long-range probe library. Subsequent detection for presence or absence of PCR products (+/– scores) is carried out either by gel electrophoresis or by internal oligonucleotide hybridizations.

The orders of the STSs relative to the genome are then determined using computational or statistical methods (M.

Boehnke, "Radiation hybrid mapping by minimization of the number of obligate chromosome breaks," *Genetic Analysis Workshop 7: Issues in Gene Mapping and the Detection of Major Genes.* Cytogenet Cell Genet, vol. 59, pp. 96–98, 1992; M. Boehnke, K. Lange, and D. R. Cox, "Statistical methods for multipoint radiation hybrid mapping," *Am. J. Hum. Genet.*, vol. 49, pp. 1174–1188, 1991; A. Chakravarti and J. E. Reefer, "A theory for radiation hybrid (Goss-Harris) mapping: application to proximal 21q markers," *Genetic Analysis Workshop 7: Issues in Gene Mapping and the Detection of Major Genes. Cytogenet Cell Genet*, vol. 59, pp. 99–101, 1992), incorporated by reference. Physical distances are then computed using maximum likelihood estimation.

In the first alternative FISH embodiment of step 7, DNA from the long-range probes (e.g., specifies-specific PCR products) are fluorescently labeled, and then hybridized back onto the genome. The fragment positions on the genome of the probes are then visualized using fluorescent microscopic imaging. Linear fractional length measurements on the metaphase spreads of chromosomes are then performed to determine the bin positions of the fragments. In the second alternative embodiment of step 7, DNA from the previously positioned bin probes is hybridized to DNA from the long-range probes.

Detailed protocols for these methods have been described (F. M. Ausubel, R. Brent, R. E. Kingston, D. D. Moore, J. G. Seidman, J. A. Smith, and K. Struhl, ed., *Current Protocols in Molecular Biology.* New York, N.Y.: John Wiley and Sons, 1995; N. J. Dracopoli, J. L. Haines, B. R. Korf, C. C. Morton, C. E. Seidman, J. G. Seidman, D. T. Moir, and D. Smith, ed., *Current Protocols in Human Genetics.* New York: John Wiley and Sons, 1995), incorporated by reference.

Referring to FIG. 1, step 9 is for producing a long-range probe library whose DNA sequences have been characterized by binning information relative to the genome.

The procedures of step 8 produce a data table which compares the DNA content of the long-range probes to bins on the genome. In the preferred embodiment, this is a table B of long-range probes (the rows of B) vs. ordered STSs (the columns of B). The pairwise distance information between the ordered STSs is also recorded. In alternative embodiments, the table can be arranged similarly.

Knowledge of the genomic positions of the RH fragments enables the desired correction of noisy RH hybridization data (discussed in step 6), as described next.

Referring to FIG. 1, step 10 is for combining the clone vs. long-range probe characterization from step 6, together with the long-range probe vs. genome binning characterization from step 9.

Figure 2:
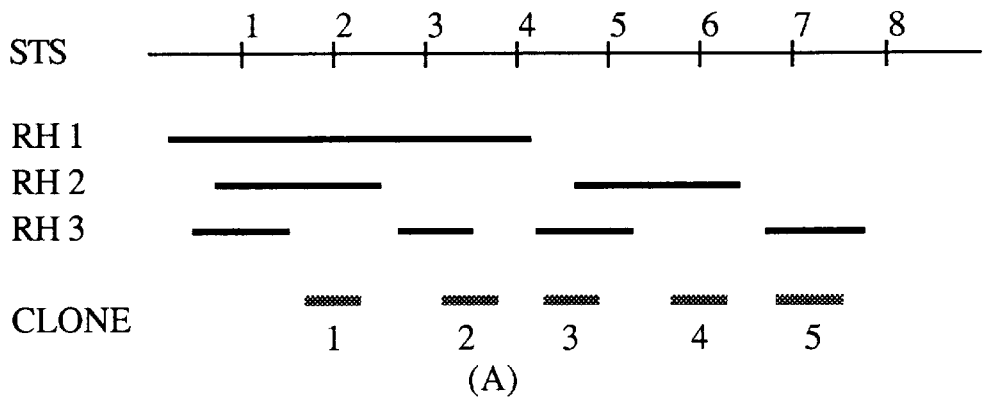
FIG. 2 is a diagram of the IPM method.
Figure 2:
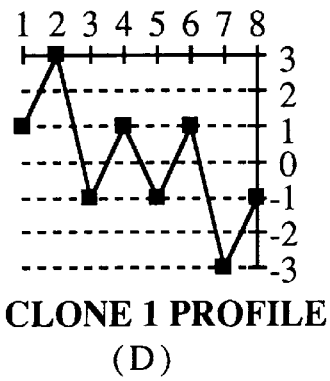

Inner product mapping is a quantitative approach to high-resolution hybridization-based RH mapping of clones (M. W. Perlin, "A system and method for producing maps and cloning genes therefrom," patent application Ser. No. 08/105,753; filed Aug. 12, 1993; M. W. Perlin, "Inner product mapping: direct localization and ordering of DNA probes using chromosome-characterized radiation hybrids," Carnegie Mellon University, Tech Report CMU-CS-92-162, June, 1992; M. W. Perlin and A. Chakravarti, "Efficient construction of high-resolution physical maps from yeast artificial chromosomes using radiation hybrids: inner product mapping," *Genomics*, vol. 18, pp. 283–289, 1993), incorporated by reference. Referring to FIG. 2, IPM localizes clones relative to RH bins by dividing the experimentation into two high-throughput subproblems (FIG. 2c): (A) clone vs. RH hybridizations, and (B) RH vs. STS PCR comparisons that genomically position the RH fragments. Data tables A and B are subsequently combined using an inner product operation (e.g., ordinary matrix multiplication) that removes the inner RH dimension (FIG. 2b). Each clone's row in the resulting matrix product is a profile of IPM scores versus chromosomally positioned STSs—the best (e.g., tallest) peak in this profile occurs at the STS (bin position) that localizes the clone on the chromosome (FIG. 2d). This localization is inferred, and does not entail direct comparison experiments between clones and STSs.

More specifically, FIG. 2 diagrams the IPM method. Referring to FIG. 2, the + score indicates a positive comparison, and − a negative comparison. (a) The actual locations of clones (lines) and STSs (points) on a chromosome that shows the STS content of each clone. Note that clones 2 and 3 hit no STS. Also shown are the locations of RH fragments. (b) Table C (clones vs. STSs) is a two dimensional representation of the actual clone sequence locations and their STS content. When both the clones and the STSs are ordered, table C is a diagonal-like matrix. STS-content mapping performs PCR comparisons between clones and STSs to directly construct table C. The * score denotes a negative STS comparison, but a positive IPM inference. (c) IPM factors table C into the two data tables A (clone vs. RH hybridizations) and B (RH vs. STS PCR assays). These two tables can be obtained separately by high-throughput experimentation, and then mathematically combined to reconstruct table C. (d) Each clone's row of RH comparison scores in table A is translated by IPM and table B into a profile along the chromosome, as sampled by the ordered STSs. The best peak of the clone's profile occurs at an STS, whose RH bin localizes the clone on the chromosome. In the idealized profile shown for clone 1, table B is not renormalized.

An inner product map integrates clones and STSs relative to RH bin positions, which is useful for sequencing and positional cloning applications. IPM can bin DNA sequences of any size. The RH clones provide multiplexed long-range coverage of a genomic region, though pools of large genomic fragments other than RHs may be used. Since each additional RH improves the localization multiplicatively, only a logarithmic number of RHs (relative to the number of STSs) is theoretically required. IPM analysis overcomes the inherent noise in RH hybridization data by redundant experimentation that uses (typically) 2–4× this minimal number of RHs. By reducing noise, IPM enables low-cost high-throughput hybridization studies to effectively map clones at high-resolution.

In the preferred embodiment, a clone's RH row vector a is combined with a STS's RH column vector b using the arithmetic inner product of vectors $$\langle a, b \rangle = \sum_{k=1}^{n} a_k b_k,$$

normalized to [−1, +1] by division with the norm $\|a\|$ or $\|a\| \cdot \|b\|$. For each clone, the clone's RH row vector a in table A is multiplied with the column-renormalized RH vs. STS table B. The computed product vector gives a profile of IPM scores versus chromosomal STS sampling locations, and the clone is localized to the STS bin in the profile which had a peak of maximum height, dubbed the IPM-max-height of the clone.

The columns of B are renormalized to compensate for unequal retention probabilities. This is done by interpreting the +/− binary scores of each column of B as {+1, −1} values and renormalizing; this gives greater weight to positive scores in columns which have fewer positive entries. For efficiency, this renormalization is computed prior to forming inner products with clone vectors. Letting $r_j$ be the probability of retaining an RH fragment in the $j^{th}$ column, the column renormalization mapped +1 to $$\frac{+1}{2r_j}, \text{ and } -1 \text{ to } \frac{-1}{2(1-r_j)}.$$

Following this transformation, the average of each column is uniformly zero, and the norms of the columns are all equal.

The inner product maximization is equivalent to least squares minimization because of this table B column renormalization. The inner product $\langle \vec{x}, \vec{y} \rangle$ can be written in terms of least-squared distances, i.e., as the $L_2$ function space norm $\|\vec{y} - \vec{x}\|_2$, as:

$$\|\vec{y} - \vec{x}\|_2 = \|\vec{y}\|_2 - 2\langle \vec{x}, \vec{y} \rangle + \|\vec{x}\|_2,$$

where $\vec{x}$ is an STS's vector of RH scores, and $\vec{y}$ is a clone's vector of RH scores. $\|\vec{y}\|_2$ is a constant of the clone data vectors $\vec{y}$. The renormalization of the table B STS column vector $\vec{x}$ sets the norm $\|\vec{x}\|_2$ to a constant, since the inner product of $\vec{x}$ with its renormalization is $$(nq)(-1)\left(\frac{-1}{2(1-r)}\right) + (np)(+1)\left(\frac{+1}{2r}\right) = n.$$

With $\|\vec{x}\|_2$ and $\|\vec{y}\|_2$ both constant, minimization of the $L_2$ norm $\|\vec{y} - \vec{x}\|_2$ corresponds to maximization of the scalar inner product $$\langle \vec{x}, \vec{y} \rangle = \sum_{i=1}^{n} x_i y_i.$$

This least-squared distance minimization approach is a proven statistical analysis technique (e.g., regression) with the advantages that it is simple, consistent (i.e., greater accuracy with additional data), and computationally efficient. Since the $L_1$ and $L_2$ norms are identical for functions whose values are restricted to {−1, 0, +1}, the technique is also robust.

In the occasional instance that there is no unique maximum because multiple peaks are identical to the maximum height, the observed versus predicted peak shape of the tied peaks are used to locate the clone to the peak (bin) having the shape closest to the expected shape. This curve fitting is carried out in a local neighborhood (such as +/−2 break distances) of the peak, and may be restricted to those neighboring points residing on a high odds RH framework map ordered with high confidence.

For comparing an observed IPM profile with its expected curve shape, it is useful to know the expected shape of an IPM peak as a function of physical map distance. Let r be the RH retention probability, λ the average break distance, θ the probability of a break, and x physical map distance. Then, with r'=1−r, the expected value of the {−1,+1} inner product is the probability of the match cases (i.e., ++ or −−) minus the mismatch cases (i.e., +− or −+):

E[IP value|θ]

=P(++|θ)+P(−−|θ)−P(+−|θ)−P(−+|θ)

=r(1−r'θ)+r'(1−rθ)−rr'θ−r'rθ,

=1−4rr'θ.

Since the renormalization used for the columns of table B constrains the adjusted retention probabilities r (and r') to uniformly equal 0.5, E[IP value|θ]=1−θ.

The RH break probability θ is related to physical map distance x via the Poisson distribution, with average break distance λ:

θ=1−$e^{-x/\lambda}$.

The expected value therefore provides the predicted functional form as a function of distance E[IP value|x]=$e^{-x/\lambda}$.

This predicted curve shape, rescaled by IPM-max-height, is used to determine the curve fit within a neighborhood of IPM scores.

In a first alternative embodiment, a maximum likelihood estimation approach is used. First, estimates of the false negative and false positive rates are made both for the clone vs. RH hybridization experiments of step 5 and for the RH vs. STS PCR experiments of step 8. These estimates are preferably indexed to RHs. These estimates can be further sharpened by indexing the error rates to genomic bins. This indexing is performed by conditioning the error rates on bins (particularly for clone vs. RH comparisons) based on an initial binning of the clones using the vector inner product described above. Second, for any RH and any bin, a contingency table of predicted STS scores vs. observed clone scores can be formed, based on the error rates. The probability of observing a pair of scores (clone vs. RH, STS vs. RH) under the assumption that the clone and STS share the same bin then corresponds to the product of a pair of error rates drawn from the contigency table. Third, for any bin, the comparison of a clone's RH scores with an STS's RH scores can be written as the product of these individual RH probabilities, based on the observed data. Fourth, maximization of the logarithm of this bin probability over all the bins (i.e., for every STS's RH scores) then localizes the clone relative to a best-fitted genomic bin.

In a second alternative embodiment, Bayesian techniques are used (J. O. Berger, *Statistical Decision Theory and Bayesian Analysis*. New York, N.Y.: Springer Verlag, 1985), incorporated by reference. A network of the parameter dependencies is constructed that models the Alu distribution along the genome and the conditional probabilities for observing data. Parameters are then estimated using Markov chain Monte Carlo methods (W. K. Hastings, "Monte Carlo sampling methods using Markov chains and their applications," *Biometrika*, vol. 57, pp. 97–109, 1970), incorporated by reference. These parameters include the bin locations of the clones.

Referring to FIG. 1, step 11 is for producing a binning of the clone library.

The procedures of step 10 produce a table which bins each clone relative to the genome. In the preferred embodiment, this is a table C of clones (the rows of C) vs. ordered bins (the columns of C). Each entry in the table describes the confidence that the clone is located in the bin.

Note that this result C is a binning of clones, not a contig. To form the desired set of mapped overlapping clones, a short-range probing is preferably performed. This probing and contig formation is performed in steps 12–16.

Referring to FIG. 1, step 12 is for obtaining a short-range probe library relative to the clone library.

Since current clone mapping technology is based on short-range probing, there is a large number of workable approaches. The preferred embodiment uses hybridization assays based on oligonucleotide probes. The design of such experiments has been described (A. J. Cuticchia, J. Arnold, and W. E. Timberlake, "PCAP: probe choice and analysis package, a set of programs to aid in choosing synthetic oligomers for contig mapping," *CABIOS*, vol. 9, No. 2, pp. 201–203, 1992; Y.-X. Fu, E. W. Timberlake, and J. Arnold, "On the design of genome mapping experiments using short synthetic oligonucletides," *Biometrics*, vol. 48, pp. 337–359, 1992; H. Lehrach, A. Drmanac, J. Hoheisel, Z. Larin, G. Lennon, A. P. Monaco, D. Nizetic, G. Zehetner, and A. Poustka, "Hybridization fingerprinting in genome mapping and sequencing," in *Genetic and Physical Mapping I: Genome Analysis*, K. E. Davies and S. M. Tilghman, ed. Cold Spring Harbor, N.Y.: Cold Spring Harbor Laboratory, 1990, pp. 39–81; A. Poustka, T. Pohl, D. P. Barlow, G. Zehetner, A. Craig, F. Michiels, E. Erlich, A.-M. Frischauf, and H. Lehrach, "Molecular approaches to mammalian genetics," in *Cold Spring Harbor Symp. Quant. Biol.*, vol. 51. 1986, pp. 131–139), incorporated by reference.

An efficient design produces 25 to 200 small (preferably 5 bp–15 bp) oligonucleotides which each hybridize, on average, to 5%–95% of the clones. The oligonucleotide sequences are generally designed to preferentially detect sequences that are related to the genes in the genome, rather than to repetitive elements in the genome or to the cloning vector. This selective bias can be achieved either by experimental probings, or by examination of the sequences to be compared. Once designed, these oligonucleotides are preferably ordered from a DNA synthesis service (Research Genetics, Huntsville, Ala.). Alternatively, they can be synthesized on a DNA synthesizer (Applied Biosystems, Foster City, Calif.).

Alternative hybridization embodiments include using clones (or their PCR products) to probe clone libraries, using pools of clones as hybridization probes, and using Southern blotting of digested clones with repetitive element hybridization probes. Enzymatic methods include gel electrophoresis of restriction endonuclease digests of clones, PCR-based STS comparisons, and hybrid methods such as Alu fingerprinting. Other short-range probes can be formed by selective or random retention of fragments produced by genome cutting.

For experimental efficiency, many of these short-range probes work in a multiplexed way, and probe one or more genome regions simultaneously. These probes include oligonucleotides, pooled clones, and repetitive-element fingerprint probes.

Referring to FIG. 1, step 13 is for comparing DNA from the clone library with DNA from the short-range probe library.

This is done by comparison experiments using standard protocols. In the preferred embodiment, DNA from the clones in the clone library is spotted onto nylon membranes. This DNA is comprised of lysed colonies, DNA preps, or species-specific PCR products. The membranes are then prepared for hybridization. Each oligonucleotide short-range probe is then labeled, preferably with $^{32}P$ using a kinase. The labeled probe is then hybridized to the membranes, followed by rinsing, stringent washing, and autoradiography. The filters may be stripped for subsequent reuse. The autoradiograph spots are then scored on a binary or more continuous (e.g., 0–255) scale.

Specific oligonucleotide hybridization protocols for particular clone libraries and oligonucleotides have been described (A. G. Craig, D. Nizetic, J. D. Hoheisel, G. Zehetner, and H. Lehrach, "Ordering of cosmid clones covering the herpes simplex virus type I," *Nucleic Acids Res.*, vol. 18, No. 9, pp. 2653–60, 1990; R. Drmanac, Z. Strezoska, I. Labat, S. Drmanac, and R. Crkvenjakov, "Reliable hybridization of oligonucleotides as short as six nucleotides," *DNA Cell Biol.*, vol. 9, No. 7, pp. 527–534, 1990; J. D. Hoheisel, G. G. Lennon, G. Zehetner, and J. Lehrach, "Use of high coverage reference libraries of *Drosophila melanogaster* for relational analysis," *J. Mol. Biol.*, vol. 220, pp. 903–914, 1991; F. Michiels, A. G. Craig, G. Zehetner, G. P. Smith, and H. Lehrach, "Molecular approaches to genome analysis: a strategy for the construction of ordered overlapping clone libraries," *CABIOS*, vol. 3, pp. 203–210, 1987; D. Nizetic, R. Drmanac, and J. Lehrach, "An improved bacterial colony lysis procedure enables direct DNA hybridization using short (10, 11 bases) oligonucleotides to cosmids," *Nucleic Acids Res.*, vol. 19, pp. 182, 1991), incorporated by reference.

For alternative short-range probes, the comparison protocols are described (see cited references above).

Referring to FIG. 1, step 14 is for producing a clone library characterized by short-range probes.

The comparison experiments of the previous step 13 construct a table D of scores that compare the DNA from clones against DNA from short-range probes. These provide measures of genomic colocalization and distance.

In this step, or in the following step 15, contigs can be formed from the short-range characterization data of the clones. In the preferred embodiment, each clone's score signature relative to the oligonucleotides is compared against other clones' score signatures. Pairs of clones having similar score signatures are inferred to be close, and their distances can be estimated. The preferred ordering method is simulated annealing (W. H. Press, B. P. Flannery, S. A. Teukolsky, and W. T. Vetterling, *Numerical Recipes in C: The Art of Scientific Computing*. Cambridge: Cambridge University Press, 1988), incorporated by reference. Effective contiging algorithms have been described (A. J. Cuticchia, J. Arnold, and W. E. Timberlake, "ODS: ordering DNA sequences, a physical mapping algorithm based on simulated annealing," *CABIOS*, vol. 9, No. 2, pp. 215–219, 1992; A. J. Cuticchia, J. Arnold, and W. E. Timberlake, "The Use of Simulated Annealing in Chromosome Reconstruction Experiments Based on Binary Scoring," *Genetics*, vol. 132, pp. 591–601, 1992; A. Milosavljevic, Z. Strezoska, M. zeremski, D. Grujic, T. Paunesku, and R. Crkvenjakov, "Clone clustering by hybridization," *Genomics*, vol. 27, No. 1, pp. 83–89, 1995), incorporated by reference.

For alternative short-range probes, the contiging analysis procedures use analogous comparison data and search procedures, and have been described (D. O. Nelson and T. P. Speed, "Statistical issues in constructing high resolution physical maps," *Statistical Science*, vol. 9, No. 3, pp. 334–354, 1994; E. Branscomb, T. Slezak, R. Pae, D. Galas, and al., "Optimizing restriction fragment fingerprinting methods for ordering large genomic libraries," *Genomics*, vol. 8, pp. 351–366, 1990; S. G. Fisher, E. Cayanis, J. J. Russo, I. Sunjevaric, B. Boukhgalter, P. Zhang, M.-T. Yu, R. Rothstein, D. Warburton, I. S. Edelman, and A. Efstratiadis, "Assembly of ordered contigs of cosmids selected with YACs of human chromosome 13," *Genomics*, vol. 21, pp. 525–537, 1994; R. Mott, A. Grigoriev, E. Maier, J. Hoheisel, and H. Lehrach, "Algorithms and software tools for ordering clone libraries: application to the mapping of the genome of *Schizosaccharomyces pombe*," *Nucleic Acids Research*, vol. 21, No. 8, pp. 1965–1974, 1993), incorporated by reference.

Referring to FIG. 1, step 15 is for combining the long-range binning of the clone library from step 11, together with the short-range probing of the clone library from step 14.

In the preferred top-down embodiment, the starting point is the binning information on the clones in the library from long-range probings. This was recorded in data table C in step 11. In every bin, the short-range probe signatures of the clones in that bin are retrieved from the data table D recorded in step 14. Using conventional contiging analysis that is highly effective on this small subset of binned clones, the short-range signatures are used to determine clone orders and distances for the contiged clones in the bin. The contigs of neighboring bins are then oriented and connected to form larger contigs. Adequate clonal redundancy ($\geq$ two-fold) assures that this process will construct very large contigs that cover most of the genome. This genomic contig is recorded in table E.

In the preferred bottom-up embodiment, the starting point is the proximity information of neighboring clones in the library from short-range probings. This was recorded in data table D in step 14. Following initial comparisons of short-range probe signatures, clusters with high confidence of clones are formed. The clone order and distances are then determined for the clones in the cluster. The long-range probe information for every clone cluster is retrieved from the data table C recorded in step 11, and a composite long-range score for the cluster is formed. In one embodiment, this composite is formed for each RH entry by taking the maximum (or other arithmetic combination) of the (clone, RH) comparison scores over all the clones in the cluster. This composite long-range score is combined with the table B information of step 9, using the IPM method described in step 10. The result is a binning of the cluster relative to the genome, and this global positioning information can be used to determine neighboring clusters. The contigs of neighboring binned clusters are then oriented and connected to form larger contigs. Adequate clonal redundancy (e.g., $\geq$ two-fold) assures that this process will construct very large contigs that cover most of the genome. This genomic contig is recorded in table E.

There are additional mixed top-down/bottom-up embodiments that use a more flexible control structure to optimize statistical properties of the data (K. V. Mardia, J. T. Kent, and J. M. Bibby, *Multivariate Analysis*. New York, N.Y.: Academic Press, 1979; D. O. Nelson and T. P. Speed, "Statistical issues in constructing high resolution physical maps," *Statistical Science*, vol. 9, No. 3, pp. 334–354, 1994; E. Rich and K. Knight, *Artificial Intelligence*. New York, N.Y.: McGraw-Hill, Inc., 1991), incorporated by reference.

A first advantage of these IPM BIN-SORT (A. V. Aho, J. E. Hopcroft, and J. D. Ullman, *Data Structures and Algorithms*. Reading, Mass.: Addison-Wesley, 1983), incorporated by reference, approaches to mapping is in the redundancy of the data acquired, and in the effectiveness of the analysis procedures in exploiting this redundancy for constructing reliable maps. Short-range and long-range data are obtained for the entire clone library. A second related advantage is in the volume of the data acquired. Note that the IPM procedure provides long-range binning information for the entire clone library. Competing binning methods only bin a small fraction of the clones and therefore produce less reliable maps. A third advantage is in the high-throughput experimentation. Both the short-range and long-range probings are done using highly parallel filter hybridizations. Further only a logarithmic number of probings is required. A fourth advantage is in the built-in validation mechanism. Comparison of long-range and short-range probing data on the clone library can detect and repair inconsistencies, as well as provide a measure of validity. A fifth advantage is in adding binning information to conventional short-range probe data. Short-range probes are inherently incapable of producing contigs covering very large genome regions since (a) the repetitive elements in a complex genome prevent extensive clone assembly, and (b) the statistical analysis becomes less reliable outside of a small (e.g., 1–2 Mb) region. Adding supplemental long-range binning information about the clones' global positionings overcomes these obstacles.

In the preferred embodiment for verifying an inner product map, the short-range probe information is used to verify and assess the long-range clone binning results. The following discussion is specialized to clone vs. clone library short-range probings, with probes such as YAC Alu-PCR products or cosmids. Each probing with a clone generates a cluster of clones, termed here "proximity group".

A map is only valuable if it is accurate. Because IPM binning can construct large-scale clone maps of previously unmapped genome regions, it may be desirable to verify the binning. Using proximity groups from clone vs. clone library hybridization, this can be done. A key point is the fact that the clones within a proximity group generally reside in identical or adjacent bins. Therefore, the groupings of the data can be cross-checked with the clone colocalizations observed in the IPM analysis.

A quantitative mechanism for assessing IPM's binning accuracy is suggested by an example. Suppose there are 10 clones in a proximity group, and that 8 of these clones cluster in the same IPM bin location. Let p be the probability that a clone is accurately localized. Then the clustering of clones observed in an proximity group has a probability distribution that enables estimation of p. Intuitively, the ratio of cluster size (i.e., 8) to group size (i.e., 10) should provide a maximum likelihood estimate (m.l.e.) of $$\hat{P} = \frac{8}{10}.$$

A better estimate of p can be computed by using all the clustering groups in forming the m.l.e.

For a given proximity group, the size n of the relevant subgroup and the size k of the largest colocalizing (by IPM) cluster of clones can be determined as a function of the parameters h, $\Delta x$, and $\Delta y$, as follows. To restrict attention to higher confidence IPM localizations, only clones in the group having IPM-max-height$\geq$h are considered; this determines the clones in the group and the group size. To determine cluster size, a token is placed in every bin that could correspond to a possible IPM bin assignment; this is done for each clone in the group by:

(1) Accounting for a clone's ambiguous IPM bin assignments (e.g., multiple peaks), and setting a (vertical) tolerance $\Delta y$. This procedure identifies one or more bins.

(2) Accounting for imprecision $\Delta x$ in bin assignments, and considering each binned peak to be localized by IPM to a range of adjacent bins [b–$\Delta x$,b+$\Delta x$], rather than to a unique IPM bin assignment b.

(3) Placing a token in every bin b identified in (1), and, depending on (2), possibly in bins adjacent to b.

A clone may contribute tokens to multiple bins, but each bin can receive at most one token from the clone. The number of tokens deposited by all the relevant IPM-localized clones is then counted at every bin. The RH bin containing the most tokens (i.e., IPM colocalizing clones) determines the size of the largest cluster.

Data on multiple proximity groups allow quantitative exploration of the accuracy of an inner product map. Let p be the probability that a randomly-chosen clone is accurately binned. While p is unknown, it can be estimated relatively easily. For a simpler case, suppose the true bin location i for each clone is known, so that it is then known that $k_i$ clustered clones were correctly classified out of the ni grouped clones that truly occur in that bin. Then the maximum likelihood estimate of p is $$\hat{p} = \frac{\sum_i k_i}{\sum_i n_i},$$

or the total number correctly classified divided by the total number examined. Of course, p cannot be estimated directly because the true locations are unknown.

To estimate p, assume that when two or more clones colocalize for both the proximity data and in the IPM map, this implies that they are classified to the correct bin (or, as assumed later, correct vicinity). This assumption is reasonable because such events rarely occur by chance. Define $k_i$ and $n_i$ as before. A complication for the analysis is that colocalization is only observed when $k_i > 2$. Thus $k_i = 0$ and $k_i = 1$ are indistinguishable, and these events must be treated jointly. By the binomial theorem, $$P(k_i < 2) = b(0; n_i, p) + b(1; n_i, p)$$

and $$P(k_i = k | k \geq 2) = b(k_i; n_i, p),$$

where $$b(k; n, p) = \binom{n}{k} p^k (1-p)^{n-k}$$

is the binomial distribution.

To estimate p, label and order the proximity groups for which there is no colocalization in the IPM data $i = 1, 2, \ldots, H$ and those showing colocalization $i = H+1, \ldots, I$. The likelihood is then given by $$\prod_{i=1}^{H} \{b(0; n_i, p) + b(1; n_i, p)\} \cdot \prod_{i=H+1}^{I} b(k_i; n_i, p).$$

While there is no closed form solution for $\hat{p}$, the m.l.e. can be obtained using standard iterative methods. Golden section search in one dimension is one applicable algorithm.

In general, the greater the IPM-max-height of a clone, the more accurately IPM has mapped it. It is therefore useful to define p(h) as the probability that a randomly-chosen clone having an IPM-max-height equal to h is accurately mapped. To obtain smooth estimates of p(h) using maximum likelihood estimation over the proximity group data, it is desirable to perform the estimation using the largest number of clones that have been mapped with the greatest confidence. This can be achieved by considering IPM-max-height on subintervals [h,1] that include the most confidently mapped clones (i.e., those clones for which h≤IPM-max-height≤1), estimating the accuracy probabilities p[h,1] with respect to these subintervals, and exploiting the property that events on intervals can be partitioned into events on disjoint subintervals, as follows.

The task is to estimate p(h), the probability that a randomly-chosen clone with IPM-max-height=h is accurately binned, and to do this using a large number of clones which have been mapped by IPM with great confidence. For any property f of the clones, and any interval [a,b] with $0 \leq a < b \leq 1$, let f[a,b] be the restriction of that property to the subset of clones having an IPM-max-height which satisfies the inequality a≤IPM-max-height≤b;

f[a,b) is similarly defined on the half-open interval [a,b). Define n[a,b] to be the number of clones satisfying "a≤IPM-max-height≤b", k[a,b] to be the number of accurately mapped clones that occur on [a,b], and note that $$\hat{p}[a, b] = \frac{k[a, b]}{n[a, b]}$$

estimates the probability of accurate mapping on [a,b].

Since k can be partitioned as k[a,c]=k[a,b)+k[b,c], one obtains $\hat{p}[a,c] \cdot n[a,c] = \hat{p}[a,b) \cdot n[a,b) + \hat{p}[b,c] \cdot n[b,c]$.

In particular, one can partition the interval [0,1] into m subintervals, each of identical size $$\Delta h = \frac{1}{m}.$$

For any height threshold $$h_j = \frac{j}{m}, 0 \leq j \leq m+1,$$

one can partition k[$h_j$,1] as $$\hat{p}[h_j, 1] \cdot n[h_j, 1] = \sum_{i=j}^{m} \hat{p}[h_i, h_{i+1}) \cdot n[h_i, h_{i+1}).$$

One can rewrite this partitioning as $$\hat{p}[h_j, 1] \cdot n[h_j, 1] = \hat{p}[h_j, h_{j+1}) \cdot n[h_j, h_{j+1}) + \sum_{i=j+1}^{m} \hat{p}[h_i, h_{i+1}) \cdot n[h_i, h_{i+1}),$$

or, solving for $$\hat{p}[h_j, h_{j+1}),$$

$$\hat{p}[h_j, h_{j+1}) = \frac{\hat{p}[h_j, 1] \cdot n[h_j, 1] - \sum_{i=j+1}^{m} \hat{p}[h_i, h_{i+1}) \cdot n[h_i, h_{i+1})}{n[h_j, h_{j+1})}.$$

Since $\hat{p}(h_j) \approx \hat{p}[h_j, h_j + \Delta h) = \hat{p}[h_j, h_{j-1})$, one can approximate $\hat{p}(h_j)$ by iterative application of this equation to the values $\{\hat{p}[h_i,1]\}$ and $\{n[h_i,1]\}$, $j \leq i \leq m$, starting from i=m. But the $\{\hat{p}[h_i,1]\}$ are readily computed by maximum likelihood estimation using the independent proximity group data, and the $\{n[h_i,1]\}$ are known.

Therefore, as required, the function p(h) can be estimated from values of $\hat{p}[h_j,1]$ that are computed on (generally) long intervals that include large numbers of confidently mapped clones.

In the preferred embodiment for refining the binning of map, note that far greater confidence can be placed in a clone's location when two independent localization data sets agree. Specifically, when a short-range proximity group has at least two clones whose long-range IPM bins agree, or at least one clone containing an STS where the clone's IPM bin agrees with the STS's RH bin, then all the clones in the group having concordant IPM localizations can be mapped with high confidence. These inferences help extend the IPM binning results to clones that have a low IPM-max-height, but which colocalize in a proximity group.

Referring to FIG. 1, step 16 is for producing a contig of the clone library which bins and orders clones relative to the genome.

The BIN-SORT process of step 15 constructs contigs of clones relative to the genome. This mapping result is recorded in a table E. In the preferred embodiment, this is a table E of clones relative to the genome locations.

Referring to FIG. 1, step 17 is for forming a tiling path of clones that span genome regions.

From an accurate clone map of a genome, a (not necessarily unique) subset of clones that cover the genome can be identified. This identification is done by starting from a leftmost clone by moving rightward from a selected clone A, selecting a neighbor B which overlaps A, and then iteratively continuing from B. A constraint can be placed on this process to find tiling paths having small or minimal length, where length is defined as the sum of the insert sizes of the component clones.

In the preferred embodiment, (minimal) tiling paths have immediately utility for finding genes. This is because the inner product map integrates genetic markers (polymorphic STSs) together with the clones that fully cover the genome region containing the gene of interest. This considerably reduces the search effort for cloning the gene. Even greater utility for positional/candidate cloning (F. S. Collins, "Positional cloning moves from perditional to traditional," *Nature Genet.*, vol. 9, No. 4, pp. 347–350, 1995), incorporated by reference, is present when a map of ESTs, expressed cDNAs, or exons is also integrated into the map.

Referring to FIG. 1, step 18 is for determining the sequence of said clones, and of the entire genome.

In the preferred embodiment, each mapped clone is selected in turn from a minimum tiling path. This clone is then subcloned into m13 sequencing vectors. For each m13 subclone, nested deletions are constructed for use in DNA sequencing. For each deletion clone, a DNA sequencing template is prepared. This template is then sequenced by the dideoxy method, preferrably using an automated DNA sequencer, such as an A.L.F. (Pharmacia Biotech, Piscataway, N.J.) or an ABI/373 or ABI/377 (Applied Biosystems, Foster City, Calif.), and 100–500 bp of sequence determined. In addition to this "shotgun" phase, in which an initial read is taken from each subclone using a universal primer, a "walking" phase takes additional reads from selected subclones by use of custom primers. Complete protocols for these and related sequencing steps have been described (F. M. Ausubel, R. Brent, R. E. Kingston, D. D. Moore, J. G. Seidman, J. A. Smith, and K. Struhl, ed., *Current Protocols in Molecular Biology*. New York, N.Y.: John Wiley and Sons, 1995; N. J. Dracopoli, J. L. Haines, B. R. Korf, C. C. Morton, C. E. Seidman, J. G. Seidman, D. T. Moir, and D. Smith, ed., *Current Protocols in Human Genetics*. New York: John Wiley and Sons, 1995).

The sequences of the nested deletion clones are assembled into the complete sequence of the subclone by matching overlaps. The subclone sequences are then assembled into the sequence of the mapped clone. The sequences of the mapped clones are assembled into the complete sequence of the genome by matching overlaps. Computer programs are available for these tasks (Rodger Staden programs, Cambridge, UK; DNAStar, Madison, Wis.). Following sequence assembly, current analysis practice includes similarity and homology searches relative to sequence databases (Genbank, Bethesda, Md.; EMBL, Cambridge, UK; Phil Green's GENEFINDER, Seattle, Wash.) to identify genes and repetitive elements, infer function, and determine the sequence's relation to other parts of the genome and cell.

Such strategies have been successfully applied to sequencing the genomes of several bacteria (Human Genome Sciences, Gaithersburg, Md.), including *E. coli* (G. Plunkett and al, "Analysis of the *Escherichia coli* genome. III. DNA sequence of the region from 87.2 to 89.2 minutes," *Nucl. Acids Res.*, vol. 21, pp. 3391–3398, 1993), incorporated by reference, and higher organisms, including yeast (S. G. Oliver and al, "The complete sequence of yeast chromosome III," *Nature*, vol. 357, pp. 38–46, 1992), incorporated by reference, human (A. Martin-Gallardo and al, "Automated DNA sequencing and analysis of 106 kilobases from human chromosome 19q13.3," *Nature Genet.*, vol. 1, pp. 34–39, 1992), incorporated by reference, mouse (R. K. Wilson and al, "Nucleotide sequence analysis of 95 kb near the 3' end the murine T-cell receptor alpha/delta chain locus: strategy and methodology," *Genomics*, vol. 13, pp. 1198–1208, 1992), incorporated by reference, and *C. elegans* (R. Wilson and al, "2.2 Mb of contiguous nucleotide sequence from chromosome III of C. elegans," *Nature*, vol. 368, pp. 32–38, 1994; J. Sulston, Z. Du, K. Thomas, R. Wilson, L. Hillier, R. Staden, N. Halloran, P. Green, J. Thierry-Mieg, L. Qiu, S. Dear, A. Coulson, M. Craxton, M. Durbin, M. Berks, M. Metzstein, T. Hawkins, R. Ainscough, and R. Waterston, "The C. elegans genome sequencing project: a beginning," *Nature*, vol. 356, pp. 37–41, 1992), incorporated by reference. The automated sequencing of large genome regions from mapped cosmid (or other) clones is now routine in several centers (Sanger Center, Cambridge, UK; Washington University, St. Louis, Mo.), with very low error at an average cost of $0.50 or less per base. Specific strategies and protocols for these efforts have been detailed (H. G. Griffin and A. M. Griffin, ed., *DNA Sequencing: Laboratory Protocols*. New Jersey: Humana, 1992), incorporated by reference.

The current best mode for sequencing is gel electrophoresis on polyacrylamide gels, possibly using fluorescence detection. Newer technologies for DNA size separation are being developed that are applicable to DNA sequencing, including ultrathin gel slabs (A. J. Kostichka, M. L. Marchbanks, R. L. Brumley Jr., H. Drossman, and L. M. Smith, "High speed automated DNA sequencing in ultrathin slab gels," *Bio/Technology*, vol. 10, pp. 78–81, 1992), incorporated by reference, capillary arrays (R. A. Mathies and X. C. Huang, "Capillary array electrophoresis: an approach to high-speed, high-throughput DNA sequencing," *Nature*, vol. 359, pp. 167–169, 1992), incorporated by reference, and mass spectrometry (K. J. WU, A. Stedding, and C. H. Becker, "Matrix-assisted laser desorption time-of-flight mass spectrometry of oligonucleotides using 3-hydroxypicolinic acid as an ultraviolet-sensitive matrix," *Rapid Commun. Mass Spectrom.*, vol. 7, pp. 142–146, 1993), incorporated by reference. DNA sequencing without the use of gel electrophoresis has also been done using sequencing by hybridization methodologies (R. Drmanac, S. Drmanac, Z. Strezoska, T. Paunesku, I. Labat, M. Zeremski, J. Snoddy, W. K. Funkhouser, B. Koop, and L. Hood, "DNA sequence determination by hybridization: a strategy for efficient large-scale sequencing," *Science*, vol. 260, pp. 1649–1652, 1993; E. M. Southern, U. Maskos, and J. K. Elder, "Analyzing and comparing nucleic acid sequences by hybridization to arrays of oligonucletides: evaluation using experimental models," *Genomics*, vol. 13, pp. 1008–10017, 1991; S. P. A. Fodor, J. L. Read, M. C. Pirrung, L. Stryer, A. T. Lu, and D. Solas, "Light-directed spatially addressable parallel chemical synthesis," *Science*, vol. 251, pp. 767–773, 1991), incorporated by reference. Another approach is base addition sequencing strategy (BASS), which uses synchronized DNA polymer construction to determine the sequence of unknown DNA templates (P. C. Cheeseman, "Method for sequencing polynucleotides," U.S. Pat. No. 5,302,509; filed Feb. 27, 1991, published Apr. 12, 1994; A. Rosenthal, K. Close, and S. Brenner, "DNA sequencing method," Patent# PCT WO 93/21340; filed Apr. 22, 1992, published Oct. 28, 1993; R. Y. Tsien, P. Ross, M. Fahenstock, and A. J. Johnston, "DNA sequencing," Patent# PCT WO 91/06678; filed Oct. 26, 1990, published May 16, 1991), incorporated by reference.

(2) Example A: Determining the Sequence of a Genome Using YACs

By combining an inner product map's long-range probing of YACs from a genome, together with short-range probing of said YACs, the method of FIG. 1 can be applied to construct contigs and then determine the DNA sequence of said genome. An example is presented for the 150 Mb human chromosome 11.

Using Alu-PCR products of chromosome 11-specific clones, serially hybridization with a set of RHs (M. R. James, C. W. Richard III, J.-J. Schott, C. Yousry, K. Clark, J. Bell, J. Hazan, C. Dubay, A. Vignal, M. Agrapart, T. Imai, Y. Nakamura, M. Polymeropoulos, J. Weissenbach, D. R. Cox, and G. M. Lathrop, "A radiation hybrid map of 506 STS markers spanning human chromosome 11," *Nature Genetics*, vol. 8, No. 1, pp. 70–76, 1994) incorporated by reference, was performed against gridded filters of Roswell Park Cancer Institute (RPCI) YACs (S. Qin, J. zhang, C. M. Isaacs, S. Nagafuchi, S. S. Jani, K. J. Abel, M. J. Higgins, N. J. Nowak, and T. B. Shows, "A chromosome 11 YAC library," *Genomics*, vol. 16, No. 3, pp. 580–5, 1993), incorporated by reference. This hybridization data was then combined with the preexisting RH map data of James et al. to build an inner product map. This binning of 865 YACs provided the first high-resolution large-scale (> two-fold redundancy) clonal coverage of human chromosome 11, and was the first inner product map ever constructed. The accuracy and precision of this chromosome 11 map was verified by performing a novel likelihood analysis relative to independent YAC hybridization data (N. Nowak, S. Qin, J. Zhang, S. Sait, M. Higgins, Y. Cheng, L. Li, D. Munroe, G. Evans, D. Housman, and T. Shows, "Generating a physical map of chromosome 11 (Abstract)," *Amer. J. Hum. Genet.*, vol. 55, No. 3 Supplement, pp. A267, 1994), incorporated by reference. These steps 1–11 are described as performed, together with details for performing steps 12–18.

The following 18 steps refer to the steps of the method of FIG. 1.
(Step 1) Obtaining a Clone Library to be Sequenced and Mapped.

The Roswell Park Cancer Institute (RPCI) chromosome 11-specific YAC library has a 350 kb average insert size (RPCI, Buffalo, N.Y.). The YACs were relatively nonchimeric, as ascertained by fluorescent in situ hybridization studies (S. Qin, J. zhang, C. M. Isaacs, S. Nagafuchi, S. S. Jani, K. J. Abel, M. J. Higgins, N. J. Nowak, and T. B. Shows, "A chromosome 11 YAC library," *Genomics*, vol. 16, No. 3, pp. 580–5, 1993), incorporated by reference.
(Step 2) Preparing DNA from Individual Clones in the Clone Library for Comparison Experiments.

DNA was prepared for PCR from 100 µl cultures of individual RPCI YAC clones, grown in AHC media in microplates as previously described (I. M. Chumakov, I. LeGall, A. Billault, P. Ougen, P. Soularue, S. Guillou, P. Rigault, Bui. H., M. F. DeTand, E. Barillot, H. Abderrahim, D. Cherif, R. Berger, D. LePaslier, and D. Cohen, "Isolation of chromosome 21-specific yeast artificial chromosomes from a total human genome library," *Nature Genet.*, vol. 1, pp. 222–225, 1992), incorporated by reference. PCR was performed in 50 µl reactions containing 5 ng YAC DNA, 50 picomoles ALE34 Alu-PCR primer (C. G. Cole, P. N. Goodfellow, M. Bobrow, and D. R. Bentley, "Generation of novel sequence tagged sites (STSs) from discrete chromosomal regions using Alu-PCR," *Genomics*, vol. 10, pp. 816–826, 1991), incorporated by reference, 200 µM dNTPs, 45 mM Tris HCl (pH 8.8), 11 mM ammonium sulfate, 2% formamide, 2 mM MgCl$_2$, 2.0 mM β-mercaptoethanol, 4.5 µM EDTA, and 1 unit Taq DNA polymerase (Boehringer Mannheim, Indianapolis, Ind.). Amplification was performed in a 9600 GeneAmp thermal cycler (Perkin Elmer, Foster City, Calif.) for 35 cycles consisting of 94° C. denaturation×60 sec, 60° C. annealing×60 sec, 72° C. extension for 150 sec, and 7 min final extension at 72° C. All PCR reactions were checked by electrophoresis on 2% agarose gels containing ethidium bromide.

Of the 1728 YACs used, 72% showed at least one unambiguous Alu-PCR band on agarose gel electrophoresis, while 23% showed no Alu-PCR bands, and 5% were equivocal. This 72–77% rate of Alu-PCR amplification was lower than the 95–99% rate expected (B. Arveiler and D. J. Porteous, "Distribution of Alu and L1 repeats in human YAC recombinants," *Mammalian Genome*, vol. 3, pp. 661–668, 1992; M. T. Ross and V. P. J. Stanton, "Screening large-insert libraries by hybridization," in *Current Protocols in Human Genetics*, vol. 1, N. J. Dracopoli, J. L. Haines, B. R. Korf, C. C. Morton, C. E. Seidman, J. G. Seidman, D. T. Moir, and D. Smith, ed. New York: John Wiley and Sons, 1995, pp. 5.6.1–5.6.34), incorporated by reference, and was most likely due to nonoptimal initial DNA preparations.

The Alu-PCR products from the 1728 YACs were gridded onto nylon filters (M. T. Ross and V. P. J. Stanton, "Screening large-insert libraries by hybridization," in *Current Protocols in Human Genetics*, vol. 1, N. J. Dracopoli, J. L. Haines, B. R. Korf, C. C. Morton, C. E. Seidman, J. G. Seidman, D. T. Moir, and D. Smith, ed. New York: John Wiley and Sons, 1995, pp. 5.6.1–5.6.34). The amplified Alu-PCR products from individual YACs from two separate PCR reactions were pooled and spotted onto Hybond N+ nylon filters (Amersham, Arlington Heights, Ill.). 1728 YACs were gridded in 3×3×96 arrays onto two filters with the 96-pin HDRT replicating tool of a Biomek 1000 workstation. DNA was immobilized by alkali fixation per manufacturer's instructions (Amersham, Arlington Heights, Ill.).
(Step 3) Obtaining a Long-range Probe Library Relative to the Clone Library.

The construction of chromosome 11-specific radiation hybrids and their use in building an RH map of chromosome 11 STSs has been previously described (C. Richard III, D. Withers, T. Meeker, S. Maurer, G. Evans, R. Myers, and D.

Cox, "A radiation hybrid map of the proximal long arm of human chromosome 11 containing the Multiple Endocrine Neoplasia Type 1 (MEN-1) and bcl-1 disease loci," *Am. J. Hum. Genet.*, vol. 49, pp. 1189–1196, 1991; C. W. Richard III and S. S. Washington, "Construction and assay of radiation hybrids," in *Current Protocols in Human Genetics*, N. C. Dracopoli, J. L. Haines, B. R. Korf, D. T. Moir, C. C. Morton, C. E. Seidman, J. G. Seidman, and D. R. Smith, ed. New York: John Wiley and Sons, 1995, pp. 3.3.1–3.3.9), incorporated by reference. 84 chromosome 11-specific radiation hybrids were developed that had an average retention probability of 0.25, with an 8 Mb average break distance (M. R. James, C. W. Richard III, J.-J. Schott, C. Yousry, K. Clark, J. Bell, J. Hazan, C. Dubay, A. Vignal, M. Agrapart, T. Imai, Y. Nakamura, M. Polymeropoulos, J. Weissenbach, D. R. Cox, and G. M. Lathrop, "A radiation hybrid map of 506 STS markers spanning human chromosome 11," *Nature Genetics*, vol. 8, No. 1, pp. 70–76, 1994), incorporated by reference.

(Step 4) Preparing DNA from Members of the Long-range Probe Library for Comparison Experiments.

PCR was performed in 50 µl reactions containing 50 ng RH DNA, 50 picomoles ALE34 Alu-PCR primer, 200 µM dNTPs, 45 mM Tris HCl (pH 8.8), 11 mM ammonium sulfate, 2% formamide, 2 mM $MgCl_2$, 2.0 mM β-mercaptoethanol, 4.5 µM EDTA, and 1 unit Taq DNA polymerase. Amplification was performed in a 9600 Gene-Amp thermal cycler for 35 cycles consisting of 94° C. denaturation×60 sec, 60° C. annealing×60 sec, 72° C. extension for 150 sec, and 7 min final extension at 72° C. All PCR reactions were checked by electrophoresis on 2% agarose gels containing ethidium bromide.

Genomic DNA from each RH was amplified with ALE34 primer PCR, then purified and concentrated with a Centricon 100 column (Amicon, Beverly, Mass.). 50 ng of probe was labeled by the random primer method per manufacturer's protocol (Ambion, Austin, Tex.).

(Step 5) Comparing DNA from the Clone Library with DNA from the Long-range Probe Library.

Serial hybridization and subsequent exposure of radio-labeled RH Alu-PCR products was done against nylon filter pairs previously gridded with Alu-PCR products of 1728 YACs. 241 RH vs. filter hybridizations were performed, with the first 146 (73 RHs×2 filters) typings augmented by 95 repeated typings. Typings were discontinued after the filters had been stripped and reused five times, by which time the inner product map was highly accurate.

The labeled RH Alu-PCR probe was preannealed with 25 ng of Cot-1 DNA (Gibco-BRL, Grand Island, N.Y.) for 2 hours at 37° C. before adding to the prehybridization mix. The nylon filters containing the spotted Alu-PCR YAC products were prehybridized overnight per manufacturer's instructions (Amersham, Arlington Heights, Ill.), except for the addition of sheared, denatured human placental DNA at a final concentration of 50 ng/ml. Filters were hybridized overnight at 68° C., washed three times with final wash of 0.1 SSPE/0.1% SDS at 72° C., before exposing to autoradiographic film for 1 to 8 days.

For every RH hybridization probing, each of the 864 YAC positions on the two autoradiographs of the gridded filters was scored on a 1–5 scale, with 1 negative, 2 equivocal, 3 weakly positive, 4 positive, and 5 strongly positive. When duplicate typings were available, the maximum of the two scores was used, since there was a very high false-negative rate in the hybridization data. This data entry was facilitated by use of an interactive computer program that presented the electronically scanned image of the filter on a computer display.

(Step 6) Producing a Clone Library Characterized by LongRrange Probes.

Table A was formed from the scorings of these 241 filter hybridizations. The scores were rescaled so that the new scaling was approximately linear, i.e., that a unit increase in the scaling indicated a unit increase in the confidence one held that the YAC actually hybridized with the RH. An equivocal event was scored as a 0, since it was equally likely to be negative or positive. A negative event was scored as −1, since there was high confidence that no observable hybridization had occurred; both positive and strongly positive events were scored as 1, since there was certainty that a hybridization event had occurred. A weakly positive event was scored at 0.67 when a single typing was available, since there was considerably more confidence that it was positive than negative, and was considered equivocal when duplicate typings were available.

(Step 7) Obtaining a Bin Probe Library Suitable for Positioning the DNA Sequences of Long-Range Probes Relative to the Genome.

506 chromosome 11-specific STSs were generated for typing against the RH library (M. R. James, C. W. Richard III, J.-J. Schott, C. Yousry, K. Clark, J. Bell, J. Hazan, C. Dubay, A. Vignal, M. Agrapart, T. Imai, Y. Nakamura, M. Polymeropoulos, J. Weissenbach, D. R. Cox, and G. M. Lathrop, "A radiation hybrid map of 506 STS markers spanning human chromosome 11," *Nature Genetics*, vol. 8, No. 1, pp. 70–76, 1994), incorporated by reference.

(Step 8) Comparing DNA from the Bin Probe Library with DNA from the Long-Range Probe Library.

The 506 chromosome 11-specific STSs were typed against 84 RHs by PCR and subsequent scoring on agarose gels. Duplicate typing experiments were performed for each (RH, STS) pair; when inconsistencies were observed a third typing was performed (M. R. James, C. W. Richard III, J.-J. Schott, C. Yousry, K. Clark, J. Bell, J. Hazan, C. Dubay, A. Vignal, M. Agrapart, T. Imai, Y. Nakamura, M. Polymeropoulos, J. Weissenbach, D. R. Cox, and G. M. Lathrop, "A radiation hybrid map of 506 STS markers spanning human chromosome 11," *Nature Genetics*, vol. 8, No. 1, pp. 70–76, 1994), incorporated by reference.

(Step 9) Producing a Long-Range Probe Library Whose DNA Sequences have been Characterized by Binning Information Relative to the Genome.

Analysis of the RH vs. STS data showed that 240 STSs fell into unique RH bins, for an average inter-bin distance of 625 kb. 73 RHs had at least 2% of scores positive relative to these 240 STS bins, which provided an estimate of the chromosomal localization of the human fragments and gaps for each RH. The 240 bins were ordered using conventional statistical RH mapping, producing a table B comparison of 73 RHs vs. 240 STSs (M. R. James, C. W. Richard Iii, J.-J. Schott, C. Yousry, K. Clark, J. Bell, J. Hazan, C. Dubay, A. Vignal, M. Agrapart, T. Imai, Y. Nakamura, M. Polymeropoulos, J. Weissenbach, D. R. Cox, and G. M. Lathrop, "A radiation hybrid map of 506 STS markers spanning human chromosome 11," *Nature Genetics*, vol. 8, No. 1, pp. 70–76, 1994), incorporated by reference. Pairwise distances were computed at adjacent bins by two-point likelihood maximization for both the 240 uniquely localizing STS markers, and 143 framework STSs.

(Step 10) Combining the Clone vs. Long-Range Probe Characterization from Step 6, Together with the Long-Range Probe vs. Genome Binning Characterization from Step 9.

An inner product map of the YACs was constructed by computationally combining table A hybridization data with table B RH map PCR data. 865 YACs were binned with high confidence by IPM relative to the high-resolution STSs, providing two-fold coverage.

Figure 3:
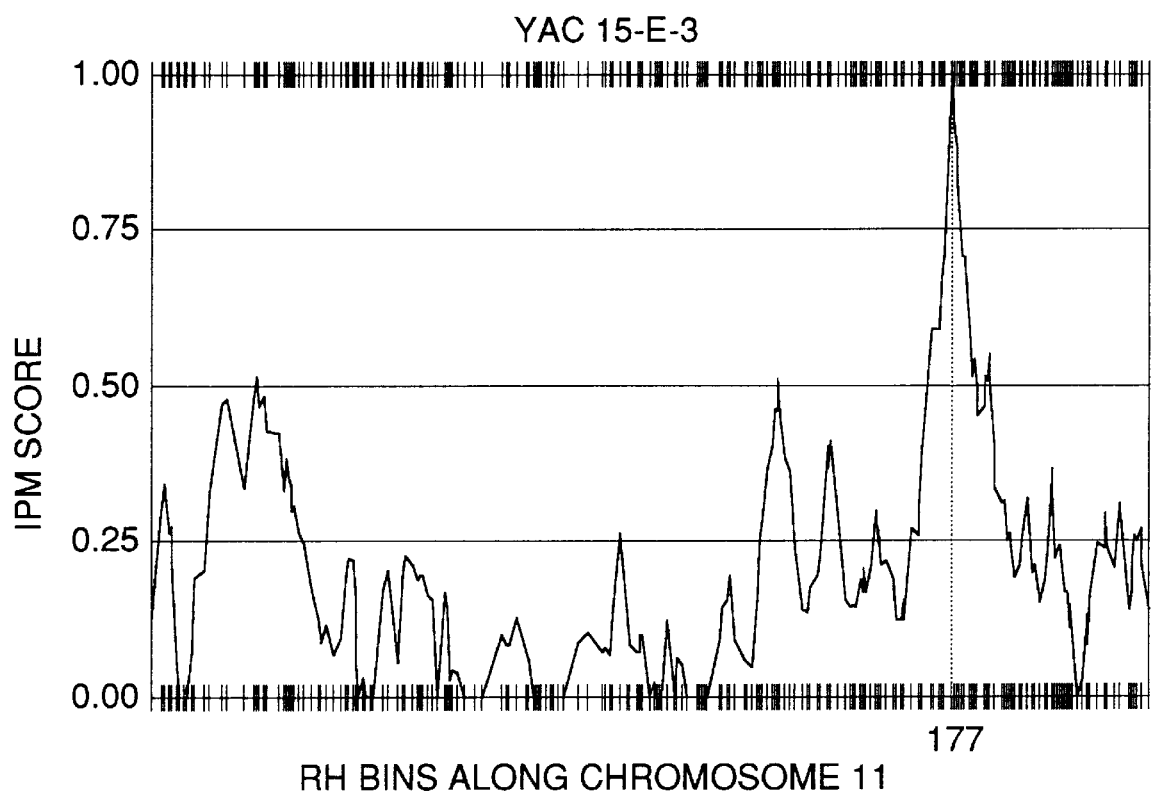
FIG. 3 is a YAC's IPM profile relative to RH bin locations along chromosome 11. Also shown is the location of the colocalizing CRYA2 STS in bin 177.

Using the analysis methods of the preferred embodiment, each column of table B was renormalized to account for unequal retention probabilities. The IPM profile of each YAC was then computed by multiplying the YAC's rescaled RH score vector in table A with the entire RH vs. STS table B matrix, and then normalizing each entry to the [−1,+1] interval. More specifically, $$\langle \underline{a}, \underline{b} \rangle = \sum_{k=1}^{n} a_k b_k,$$

with n=73 RHs, normalized to [1,+1] by division with the norm $\|\underline{a}\|$. This inner product operation transformed each YAC's observed RH hybridization vector into a computed chromosomal localization profile, as sampled by ordered STSs on the RH map. Referring to FIG. 3, the best (e.g., tallest) peaks of this profile indicated candidate bin locations for the YAC.

Referring to the following table, in the occasional instance that there was no unique maximum because multiple peaks were identical to the maximum height, the observed versus predicted peak shape of the tied peaks was used to locate the YAC to the peak (bin) having the shape closest to the expected shape. This curve fitting was carried out in a local neighborhood (+/−2 break distances) of the peak, using only those neighboring points residing on the 1000:1 odds RH framework map comprised of 143 bins ordered with high confidence. Matrix and statistical processing was performed in Macintosh Common LISP (Digitool, Cambridge, Mass.) and Excel (Microsoft, Redmond, Wash.).

Table of ambiguities introduced by considering nonmaximum IPM values. To improve the odds of accurately binning a YAC, IPM values that are (less than but) close to the YAC's IPM-max-height may be considered; these values may ambiguously localize the YAC to multiple RH bins. A height tolerance Δy is set which introduces an ambiguity for considering all the STS bins having IPM values exceeding (1−Δy)×IPM-max-height. For example, with Δy=0.05, there is an average localization to 1.75 bins (instead of to one unique bin). The ambiguity dependence as a function of IPM height threshold was computed for high confidence YACs (IPM-max-height≧0.5). Computation for YAC subsets having different ranges of IPM-max-height showed that the ambiguity was Krelatively independent of IPM-max-height.

| Δy | best | 0.00 | 0.01 | 0.02 | 0.05 | 0.10 | 0.15 | 0.20 | 0.25 |
|---|---|---|---|---|---|---|---|---|---|
| ambi-guity | 1.00 | 1.05 | 1.20 | 1.30 | 1.75 | 2.85 | 4.08 | 5.52 | 7.10 |

Referring to the following table, a reliable predictor of IPM's mapping efficacy was found to be the maximum IPM value (IPM-max-height) appearing in a YAC's IPM profile, where 0≦IPM-max-height≦1.

Table of number of YACs mapped vs. IPM-max-height. The confidence in IPM's binning accuracy increases with a YAC's IPM-max-height value. For each threshold height h, the number of YACs that have IPM-max-height≧h is given for our chromosome 11 IPM results. Roughly 1-fold coverage is achieved at threshold h=0.5, and 2-fold coverage at h=0.3.

| h | number of YACs |
|---|---|
| 1.0 | 14 |
| 0.9 | 49 |
| 0.8 | 145 |
| 0.7 | 262 |
| 0.6 | 382 |
| 0.5 | 508 |
| 0.4 | 642 |
| 0.3 | 817 |
| 0.2 | 1022 |
| 0.1 | 1319 |

Visual inspection was performed on the first 500 YACs, sorted in decreasing IPM-max-height order. Referring to FIG. 3, the inspection assessed IPM profile, concordance of IPM binning with independent physical mapping data, and statistical properties (e.g., curve fit to expected peak shape). Inner product mapping localizations were then computed for the 1319 YACs associated with Alu-PCR signals having IPM-max-height≧0.1. The YACs were localized to those RH bins having the greatest IPM value(s).

To unambiguously bin a YAC, the bin location corresponding to the IPM-max-height was selected. However, this bin choice was not always correct. Moreover, more than one likely bin location could appear in the IPM profile. This ambiguity could be due to low copy repeats, chimerism, nonuniform Alu distribution, competition between Alu sites during PCR amplification, low YAC DNA quality, or other errors affecting the hybridization data. Consideration was therefore directed to a set of most likely bin locations, thus increasing the likelihood of including the actual chromosomal bin in our selection. Allowing for greater ambiguity, a height tolerance Δy could be set which included all RH bins having IPM height values exceeding (1−Δy)×IPM-max-height. On average, there was little ambiguity (i.e., fewer than two bins) when Δy was less than 0.05.

(Step 11) Producing a Binning of the Clone Library.

The inner product mapping binning strategy was applied to human chromosome 11 by performing 241 gridded YAC filter hybridization experiments to construct table A, and combining this data with pre-existing table B radiation hybrid mapping data. Subsequent IPM analysis constructed a table C map of the 150 Mb chromosome having two-fold coverage in 350 kb (average) YACs relative to 240 uniquely binned STSs spaced 625 kb (average) apart. Comparison of these accurately localized YACs with the 111 highly informative genetic markers binned to the same 240 RH map loci is extremely useful for positional cloning studies.

(Step 12) Obtaining a Short-Range Probe Library Relative to the Clone Library.

The RPCI YAC library served as the source of short-range probes.

(Step 13) Comparing DNA from the Clone Library with DNA from the Short-range Probe Library.

RPCI performed 1,007 Alu-Alu hybridization probings of RPCI YACS against a gridded RPCI YAC library (N. Nowak, S. Qin, J. Zhang, S. Sait, M. Higgins, Y. Cheng, L. Li, D. Munroe, G. Evans, D. Housman, and T. Shows, "Generating a physical map of chromosome 11 (Abstract)," Amer. J. Hum. Genet:., vol. 55, No. 3 Supplement, pp. A267, 1994), incorporated by reference. These experiments yielded groups of proximate YACs which were largely unpositioned. While these proximity groups did not constitute a complete map, the short-range probings are useful for constructing contigs and for determining the accuracy of the inner product map. Those YACs not used in the IPM experiments and singleton groups were eliminated. This filtering yielded 400 RPCI proximity groups containing 1216 YACs with IPM-max-height≧0.1.

(Step 14) Producing a Clone Library Characterized by Short-range Probes.

The result of the step 13 hybridization comparisons is a table D that contains short-range probing data on the RPCI YACs. Each element of this table is the set of YACs forming one RPCI proximity group.

This short-range data can be used to estimate clone orders and distances for proximate clones. Existing analysis methods provide useful approximations (S. G. Fisher, E. Cayanis, J. J. Russo, I. Sunjevaric, B. Boukhgalter, P. Zhang, M.-T. Yu, R. Rothstein, D. Warburton, I. S. Edelman, and A. Efstratiadis, "Assembly of ordered contigs of cosmids selected with YACs of human chromosome 13," *Genomics*, vol. 21, pp. 525–537, 1994; R. Mott, A. Grigoriev, E. Maier, J. Hoheisel, and H. Lehrach, "Algorithms and software tools for ordering clone libraries: application to the mapping of the genome of *Schizosaccharomyces pombe*," *Nucleic Acids Research*, vol. 21, No. 8, pp. 1965–1974. 1993), incorporated by reference. With large variations in clone size, insert size information can exploited to compute more accurate determinations, as described next.

This preferred embodiment determines a fine-grained map of a contig from clone vs. clone library comparison and clone size data. To estimate the distance between two clones A and B, first consider the conditional probability that clones A and B both intersect a clone C, given that at least one of A or B intersects C. Let lenA, lenB, and lenC denote the lengths of the three clones, respectively. Let d be the distance between the centers of clones A and B.

The total genome length over which either A or B can intersect C is $$lenA+lenB+2lenC$$

when d>lenA/2+lenB/2+lenC, and is $$(lenA+lenC)/2+d+(lenB+lenC)/2$$

when d≦lenA/2+lenB/2+lenc. Setting the quantity $$e=(lenA+lenB+2lenC)/2,$$

the total length is therefore:

$$e+\min(d,e).$$

The total genome length over which both A and B can intersect C, is by similar reasoning:

$$e-\min(d,e).$$

Therefore, the required conditional probability is the ratio of these two numbers, or, as a function of the distance d, $$P(A\cap C\wedge B\cap C|A\cap C\vee B\cap C)=[e-\min(d,e)]/[e+\min(d,e)].$$

A probe C that is identical to either clone A or clone B is handled as a simpler special case.

The joint probability as a function of distance d between A and B relative to a set of short-range clones $\{C_i\}$ that independently probe the library containing A and B is therefore the product of the probabilities $$P(A\cap C_i\wedge B\cap C_i|A\cap C_i\vee B\cap C_i),$$

where the index i is restricted to just those clones $C_i$ that intersect either clone A or clone B. Maximizing the logarithm of this joint probability by varying d using a fixed probe data set will compute the m.l.e. of d, i.e., an estimate of the distance between the centers of clones A and B.

An ordering of the clones can be computed using these pairwise m.l.e. distances. In one preferred embodiment, the sum of pairwise distances is formed assuming a given ordering. As this ordering is varied, so too does the computed sum of pairwise distances. Using simulated annealing as a preferred search engine, an ordering of clones can be found which heuristically minimizes the computed sum. The resulting orders and distances between the clones provide a fine-grained map of the contig. An example of this preferred fine-mapping procedure is shown for chromosome 11 data in step 16 below.

In another preferred embodiment, the orders and distances are refined using multi-clone likelihood estimation, starting from the two-clone map estimate. This refinement is done by noting that the total length of the intersection of n clones with respect to a probe clone C can be written as the greater of 0 or:

min(right end points of the broadened clones)−max(left end points of the broadened clones), where a "broadened clone" uses the line segment representing the clone, but has the quantity lenC/2 added to its right end point, and subtracted from its left end point. Note that the measure of a union of events can be written as a sum of intersections by the method of inclusion and exclusion (W. Feller, *An Introduction to Probability Theory and Its Applications*, vol. I, Third Edition. New York: John Wiley & Sons, 1968), incorporated by reference. Thus, the ratio of the measure of intersection to the measure of union can be formed, which calculates the conditional probability of the observed intersection/nonintersection (+/−) pattern of the n clones with a probe clone C, assuming fixed distances between the mapped clones. A joint probability is then formed as a product of these independent clone probings. Clone orders are then compared by multipoint analysis, with clone distances refined by a multidimensional search over the joint distance space.

In an alternative embodiment, the positions of the centers of the clones are computed by maximizing a likelihood function constructed from a data error model of overlap. Assume an initial ordering and distances between the centers of adjacent clones, possibly constructed using the preferred fine-mapping embodiment. This predicted model can then be compared with the observed short-range overlap data. Overlap is predicted when the distance between the center of two clones is less than or equal to the sum of the radii of the two clones. An m×n table of m probes vs. n clones specifying these predictions can be constructed, and compared against the observed data. The probabilities of the 2×2 contingency table are derived from the error rate (false negatives and positives) of the comparison experiment. For example, the probability of predicting an overlap and observing an overlap is the probability of a true positive. The logarithm of the product of the resulting m×n probabilities then serves as a (possibly heuristic) likelihood function. Maximization of the likelihood relative to the probe data can then estimate the positions of the centers of the clones. This estimation produces a fine-grained map of the clones in the contig.

(Step 15) Combining the Long-range Binning of the Clone Library from Step 11, Together with the Short-range Probing of the Clone Library from Step 14.

The BIN-SORT approach is used to construct a contic of the RPCI YACs. In the preferred embodiment, the long-range inner product map of the YACs is combined with the short-range YAC vs. YAC comparison data. This combination produces relative ordering and distance information for the contiged RPCI YACs on chromosome 11.

These short-range data can also be used for verification of the inner product map binning results. The 400 RPCI proximity groups containing 1216 YACs were used for a verification analysis. The YACs within an RPCI proximity group generally reside in identical or adjacent bins. Therefore, the groupings of the RPCI data could be cross-checked with the YAC colocalizations observed in the IPM analysis. When comparisons were made between IPM's predicted bin locations and the independent RPCI data, IPM binning, RPCI proximity group, and (limited) STS-content location were found to be highly concordant in most regions.

Figure 4:
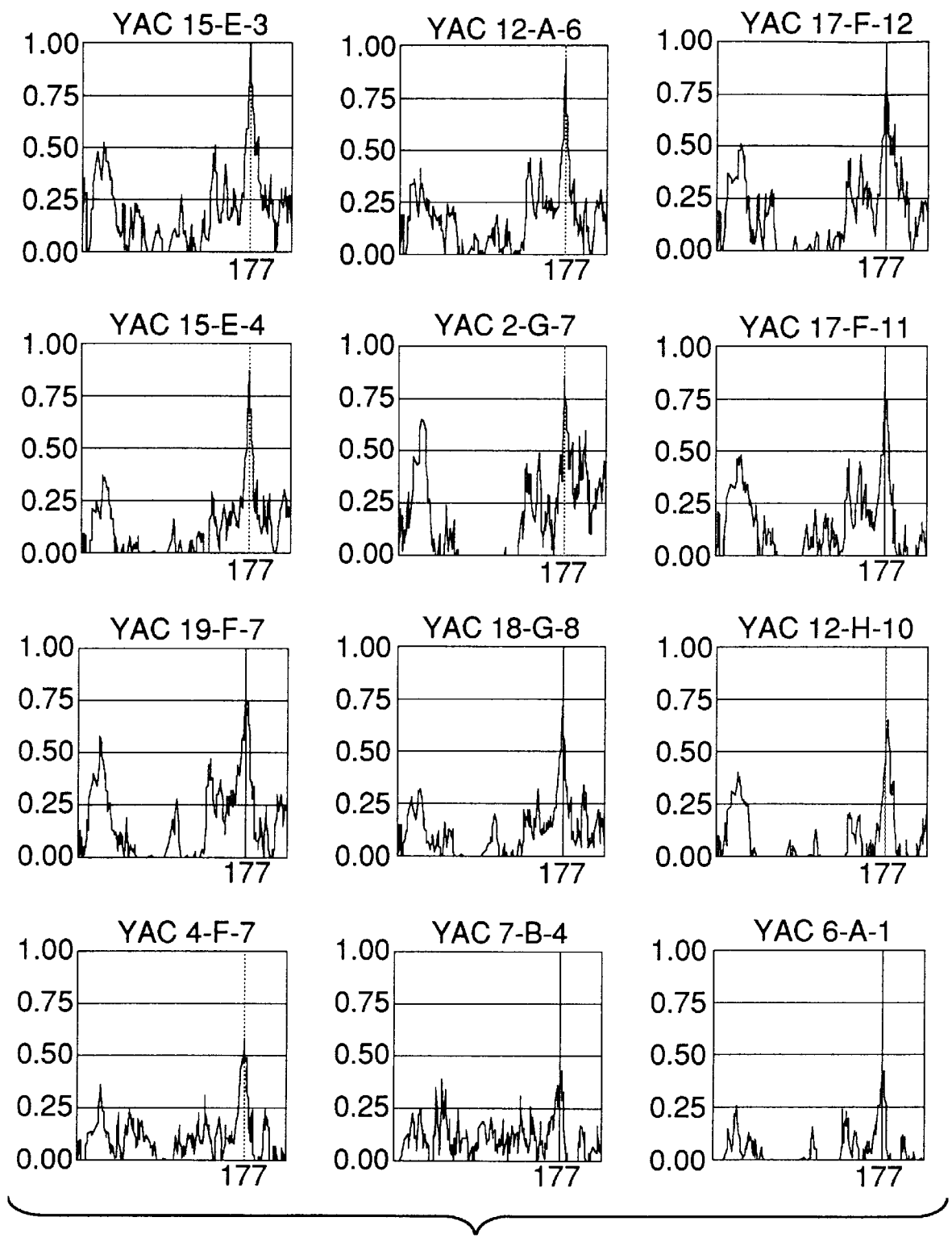
FIG. 4 is a set of profiles for twelve colocalizing RPCI YACs.

Referring to FIG. 4, the quantitative mechanism for assessing IPM's binning accuracy was highlighted by the clustering of the 12 YAC IPM bin locations in a group of 13 proximate YACs. These 12 YACS are all localized by IPM to lie on or near RH bin position 177 (of 240 bins). The gene CRYA2 is contained in three of these YACs, and was independently binned to position 177 on the RH map. Let p be the probability that a YAC is accurately localized. Then the clustering of YACs observed in an RPCI group has a probability distribution that enables estimation of p. For example, in the CRYA2 clustering shown, the ratio of cluster size (i.e., 12) to group size (i.e., 13) provides a maximum likelihood estimate (m.l.e.)

$$\hat{p} = \frac{12}{13}.$$

For each RPCI proximity group, the size n of the relevant subgroup and the size k of the largest colocalizing (by IPM) cluster of YACs were determined as a function of the parameters h, $\Delta x$, and $\Delta y$, as described in the preferred embodiment. The functions p[h,1] were computed using these RPCI proximity group data. From this set, the useful function p(h) was derived, which estimates the probability that a YAC with a given IPM-max-height value is accurately localized. Since p(h) was closely approximated by a straight line, the quantitative verification results are summarized for a range of preset tolerances $\Delta x$ and $\Delta y$ in terms of these fitted lines in the following table.

Table of linear fitting of accuracy vs. IPM-max-height. For varying values of the ambiguity tolerance $\Delta y$ and the bin resolution $\Delta x$, the estimated probability $\hat{p}(h)$ of accurate IPM YAC binning was computed as a function of YAC IPM-max-height h, $0.1 \leq h < 0.9$. The relation is almost linear, so the results are summarized here by the fit of the function to the linear model p=a+bh, along with the computed $r^2$ value. At $h \leq 0.9$, p is fixed at 1.0, so larger p-intercept values of a (or, equivalently, smaller slope values of b) imply greater probabilities at all values of h. As the tolerable uncertainties $\Delta x$ or $\Delta y$ are increased, so does the estimated probability of accurate mapping.

|  |  | bin resolution $\Delta x$ | | |
|---|---|---|---|---|
|  |  | +/− 1 | +/− 2 | +/− 4 |
| ambiguity tolerance $\Delta y$ | 0.00 | a = 0.154<br>b = 0.950<br>$r^2$ = 0.973 | a = 0.228<br>b = 0.889<br>$r^2$ = 0.976 | a = 0.338<br>b = 0.762<br>$r^2$ = 0.980 |
|  | 0.05 | a = 0.220 | a = 0.308 | a = 0.397 |

-continued

|  | bin resolution $\Delta x$ | | |
|---|---|---|---|
|  | +/− 1 | +/− 2 | +/− 4 |
|  | b = 0.903<br>$r^2$ = 0.977 | b = 0.805<br>$r^2$ = 0.976 | b = 0.692<br>$r^2$ = 0.986 |
| 0.10 | a = 0.297<br>b = 0.824<br>$r^2$ = 0.970 | a = 0.381<br>b = 0.727<br>$r^2$ = 0.963 | a = 0.461<br>b = 0.625<br>$r^2$ = 0.984 |

Figure 5:
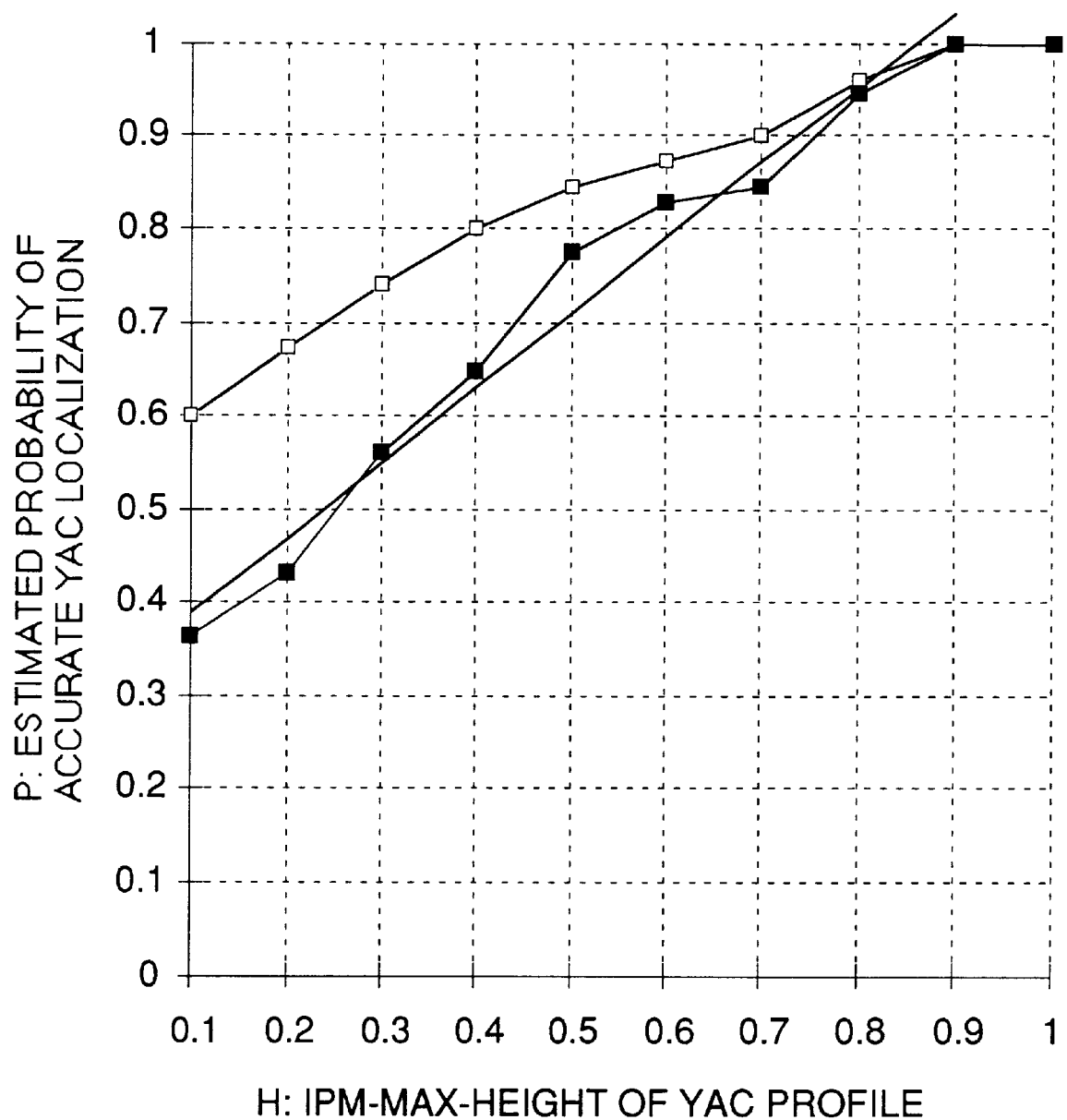
FIG. 5 is a set of curves that show the probability that a YAC is accurately localized.

Referring to FIG. 5, shown is $\hat{p}(h)$, the estimated probability that a YAC is accurately localized, as a function of the IPM-max-height threshold h, computed with parameters $\Delta x=2$ and $\Delta y=0.05$. The curves were generated by analyzing clusters at each value of h shown relative to independent RPCI proximity group data. The first curve (white squares) is the function p[h,1]. The second curve (black squares) is the function $\hat{p}(h)$, computed from $\hat{p}[h,1]$ by iterative differencing. The third curve (line without markers) was computed by a linear fit to $\hat{p}(h)$, for $0.1 \leq h \leq 0.9$. Note that the probabilities for h=0.5 and h=0.6 curve up above the fitted line; this pattern is generally observed regardless of the parameter choices $\Delta x$ and $\Delta y$.

For greater confidence in the YAC'S location, the short-range probing data were applied to the long-range IPM binning results to for agreement between these two independent data sets. These inferences extended the IPM binning results to YACs that had a low IPM-max-height, but which colocalized in an RPCI group. In the following table, the inner product map of 865 chromosome 11 YACs reported IPM binning results for all YACs with IPM-max-height$\geq 0.5$, and for those YACs with $0.1 \leq$IPM-max-height$<0.5$ that were highly concordant with RPCI proximity group data.

Table of IPM binning for 865 RPCI YACs. IPM binning is shown for a subset of 865 YACS (2.02-fold coverage) that were checked with RPCI hybridization proximity group and STS-content data. Within each of these 196 occupied bins (82% of the 240 RH map bins), the YACs are listed in descending rank order. The YAC name (RPCI plate accession id number) is shown together with its IPM-max-height value (in percent), to indicate the relative confidence in IPM's RH bin assignment. Parentheses indicate disagreement with RPCI data. The YACs were binned with ambiguity $\Delta y=0.05$ and resolution $\Delta x=+/-4$ bins, so one YAC may localize to more than one bin. With closely neighboring (+/−4) bins, only the best bin is listed (1014 listings appear for the 865 YACs). When using the table for positional cloning, it is generally advantageous to consider YACs in neighboring bins, and reference should be made to the physical distances and binned STSs on the RH map. Of the 508 YACs binned by IPM with high confidence ($0.5 \leq$IPM-max-height), 423 YACs were not inconsistent with the RPCI group and STS-content data, while 85 YACs (indicated in parentheses) were inconsistent. Of the 842 lower confidence YACs ($0.1 \leq$IPM-max-height$<0.5$), the 357 YACs having IPM colocalizations consistent with the RPCI data are listed. The breakpoint of h=0.5 for "high confidence" YACs was chosen based on the probability curve shape: the probabilities at h=0.5 are near p=0.8, but fall off sharply at h=0.4. The consistency analysis was done using the 1319 YACs associated with Alu-PCR products (IPM-max-height$\geq 0.1$).

| bin number | YAC clone ids with IPM-max-height values |
|---|---|
| 177 | 15E3:100, 12A6:93, 17F12:91, 17H4:87, 15E4:86, 17F11:83, (3F3:83), 18G8:79, 2E5:78, 7D5:71, 19C10:70, 4H7:65, 4F7:56, 14F9:43, 6A1:42, 9F2:32, 11B12:19 |
| 178 | 14A1:97, 13H12:88, 18B1:86, 18B5:84, 19F7:83, (12E10:63), 7C6:57, 18C11:25 |
| 179 | 2G7:86, 12E11:83, 18C6:75, 11B9:68, 17C10:63, 19G12:59, 12C1:44 |
| 180 | 14E10:77 |
| 181 | (18A3:77), (12F11:74), 15H6:64, 12D3:53, 7B4;42, 19H12:38, 7F1:27 |
| 182 | 12H10:64 |

Quantitative verification methods on independent proximity data were used to compute probability estimates for binning accuracy (as a function of each YAC's IPM-max-height) relative to ambiguity and resolution parameters. These verification methods were applied to the chromosome 11 IPM data, and demonstrated 72–75% accuracy of IPM binning of 642 YACs (with $\Delta x$=625 kb, $\Delta y$=0.0), of 817 YACs (with $\Delta x$=1.25 Mb, $\Delta y$=0.05), and of 1022 YACS (with $\Delta x$=2.5 Mb, $\Delta y$=0.10). A high-confidence map of 865 YACS that checked IPM localizations against independent YAC hybridization and STS-content data was tabulated in the preceding table. IPM's mapping efficiency was 66%: 865 YACs were binned out of 1319 YACs that were associated with Alu-PCR signals.

(Step 16) Producing a Contig of the Clone Library Which Bins and Orders Clones Relative to the Genome.

As an example of the preferred fine-grained mapping embodiment, 13 chromosome 11 YACs were binned by both IPM and STS-content, with additional hybridization data, to the CRYA2 bin #177 neighborhood. Following this long-range binning, the short-range comparison data was used to compute pairwise m.l.e. distances. Minimization of the sum of the distances by simulated annealing inferred the following relative positions (orders and distances) of the YACs within the bin. Here, the YAC name is given in RPCI plate coordinates, "pairwise" refers to the pairwise distance (in kb) between the YACs on the listed and preceding lines, "running" refers to the running distance (kb) within the contig up to the listed YAC, and "size" gives the insert size of the listed YAC (kb). This fine-grained mapping result showed complete concordance with RPCI's independent contig analysis.

| YAC | pairwise | running | size |
|---|---|---|---|
| 4h7 | — | 0 | 325 |
| 4f7 | 0 | 0 | 275 |
| 6a1 | 191 | 191 | 275 |
| 7b4 | 53 | 244 | 325 |
| 15e4 | 45 | 289 | 275 |
| 17h4 | 58 | 347 | 875 |
| 17f11 | 0 | 347 | 475 |
| 17f12 | 0 | 347 | 475 |
| 15e3 | 44 | 391 | 450 |
| 19f7 | 48 | 439 | 775 |
| 3g9 | 587 | 1026 | 300 |
| 12h10 | 0 | 1026 | 325 |
| 2g7 | 142 | 1168 | 425 |

This contiging procedure is used on every IPM bin. First, the YACs within the bin are retrieved. Second, the short-range comparison data is retrieved for each YAC in the bin. Third, the fine-grained mapping method is applied to the short-range comparison data on these YACs to estimate orders and distances of the YACs within the bin. This procedure is performed on every bin in the inner product map, constructing a fine-grained mapping of the YACs in every bin. Errors are detected by the exclusion of a YAC from its neighbors in the bin; these misbinned YACs are processed only locally as if they had not been binned. The contigs from each bin are then joined by short-range comparison of end clones. This constructs table E, which positions every YAC relative to the chromosome and its neighbors.

In an alternative embodiment, the RCPI hybridization proximity group is first collectively binned by forming a composite RH score vector for the clone set, together with the RH vs. STS table B, using IPM analysis. This binned set of YACs is then formed into a contig having computed orders and distances by use of the short-range comparison data. This constructs table E, which positions every YAC relative to the chromosome.

(Step 17) Forming a Tiling Path of Clones that Span Genome Regions.

From the contig formed in step 16, a path of YAC clones that tiles the mapped portions of chromosome 11 is identified and selected.

(Step 18) Determining the Sequence of Said Clones, and of the Entire Genome.

Each of the YAC clones selected in step 17 is used to probe the chromosome 11 cosmid library (Los Alamos). The YAC probe is constructed by IRE-PCR of the YAC DNA, is labeled by the random primer method, and is hybridized to a gridded cosmid library in order to identify the set of cosmid clones that colocalize with this YAC's chromosome bin. This small set of cosmids is readily contiged using restriction fingerprinting (A. Coulson, J. Sulston, S. Brenner, and J. Karn, "Toward a physical map of the genome of the nematode *Caenorhabditis elegans*," *Proc. Natl. Acad. Sci. USA*, vol. 83, pp. 7821–7825, 1986; M. V. Olson, J. E. Dutchik, M. Y. Graham, G. M. Brodeur, C. Helms, M. Frank, M. MacCollin, R. Scheinman, and T. Frank, "Random-clone strategy for genomic restriction mapping in yeast," *Proc. Natl. Acad. Sci. USA*, vol. 83, pp. 7826–7830, 1986; Y. Kohara, K. Akiyama, and K. Isono, "The physical map of the whole E. coli chromosome: Application of a new strategy for rapid analysis and sorting of a large genomic library," *Cell*, vol. 50, pp. 495–508, 1987), incorporated by reference, or oligonucleotide hybridization. The use of cosmid contiging facilitates the subsequent sequence assembly. The DNA sequence of each cosmid is determined using standard methods. These contiged cosmid sequences are then assembled into the DNA sequence of the YAC's DNA insert. Performing this operation for every selected YAC determines the sequence of the YAC-covered regions of chromosome 11.

(3) Example B: Determining the Sequence of a Genome Using Cosmids

Referring to FIG. 1, an example method is described for sequencing genomes using cosmids that is comprised of the steps:

(1) Obtaining a cosmid library that is to be sequenced and mapped from the Los Alamos national laboratory, or from one of the NIH or DOE genome centers. These libraries generally have five-fold coverage of a chromosome. Alternatively, a cosmid library can be constructed (J. Sambrook, E. F. Fritsch, and T. Maniatis, *Molecular Cloning, Second Edition*. Plainview, N.Y.: Cold Spring Harbor Press, 1989), incorporated by reference.

(2) Preparing DNA from individual clones in the cosmid library for comparison experiments. This is done by growing up cosmid colonies and lysing them, or by making Qiagen DNA preps. The cosmid DNA is then spotted onto nylon membranes from 96-well plates in a 4×4 multiplexing using a BioMek robot (Beckman Instrument, Fullerton, Calif.) or in a 3×3 multiplexing using a 96-pin metal filter frame replicating tool (Washington University Machine Shop, St. Louis, Mo.). Controls are included on the membrane for automated computer analysis, including positioning and scoring.

(3) Obtaining a radiation hybrid library relative to the cosmid library. In the preferred embodiment, this is done using the whole genome RHs (Stanford or European Consortium) that are commercially available (Research Genetics, Huntsville, Ala.). For many mammalian chromosomes, chromosome-specific RH sets have been constructed. Alternatively, RH sets can be constructed using standard protocols, as described.

(4) Preparing DNA from members of the RH library for comparison experiments. This is best done using the hybridization IRE-bubble PCR protocol (David Munroe, Cambridge, Mass.). In this protocol, four different short cutting (4 bp and 6 bp) restriction enzymes are used in separate reactions to digest the RH source DNA. Then, the annealed bubble linkers are ligated onto the fragments. After the PCR template has been prepared, separate amplifications with three different Alu primers and the bubble primer on each of the four templates is performed. The 12 PCR products are then pooled, and a fill-in reaction is done to prepare for ligation. A kinase/ligase reaction is then performed to construct concatamers, which increases signal-to-noise in the later hybridization step. Labeling is then done on lul of DNA product by random priming.

(5) Comparing DNA from the cosmid library with labeled DNA from the RH library. DNA hybridization of the RH probes to the gridded cosmids is performed on nylon membranes as described.

(6) The cosmid library is then characterized by the RHs. The data may be rescaled, as described.

(7) STSs are used as the bin probe library. These have been constructed at 1Mb resolution for the entire human genome (Whitehead Institute Genome Center, Cambridge, Mass.). Some are made polymorphic (e.g., polynucleotide repeat markers) if positional cloning is a desired feature of the final map. Alternatively, new STS probes can be readily constructed from random clones. For many RHs, these STSs already exist and have been typed.

(8) Comparing DNA from the STS bin probe library with DNA from the RH long-range probe library is done by PCR. The RH DNAs are prepared and aliquoted into the wells of a 96-well plate. Then, the STS' oligonucleotides are added to the PCR mixture, and all the RHs are amplified simultaneously on a multi-well thermocycler. The PCR products are then run out separately on an agarose gel. Visualization of the expected band leads to a + score, whereas nonvisualization leads to a − score. Experiments are done in duplicate, with ties broken by a third experiment.

(9) The RH vs. STS data is then analyzed using conventional RH mapping software such RH-Map (Michael Boehnke, Ann Arbor, Mich.). This produces an RH library whose DNA fragments have been characterized by STS binning information relative to the genome. For the human WG-RHs, table B data or mapping services are available on-line for both the Stanford RH set (shgc- (www.stanford.edu WWW site) and the European Consortium RH set (www.edi.ac.uk WWW site).

(10) The cosmid vs. RH table A data from step 6 is combined with the RH vs. STS table B data from step 9. This is done using an arithmetic matrix product operation to build an inner product map.

(11) The IPM analysis produces a global binning of most of the cosmids in the library.

(12) A set of 25–200 oligonucleotides (6 bp–15 bp) are designed for optimal experimentation and analysis on the 40 kb cosmid library. The PCAP program (or its mechanisms) can be helpful in this design.

(13) The cosmid library is gridded onto nylon membranes, as described. Each oligonucleotide in the short-range library is serially labeled and hybridized against the gridded membranes. The membrane images are formed using either autoradiography or electronic developing, and then scored and recorded. The scoring can be done manually, or with the assistance of scoring software.

(14) The oligonucleotide hybridization data on the cosmid library is then stored in the memory of a computing device. This short-range probe data is available as needed for assembling the detailed contig map.

(15) Every bin on the inner product map from step 11 is then analyzed. The cosmid set is retrieved from each bin, along with each cosmid's oligo hybridization data from step 14. Sorting is done using this short-range data to produce a fine-grained contig map (including orders, distances, and overlaps) of the cosmids. The contig maps of adjoining bins are combined to contig the entire genome.

(16) The BIN-SORT operation of step 15 produces a contig of the cosmid library which bins and orders the cosmids relative to the genome.

(17) A short tiling path of cosmids having small total length is then selected that spans large regions of the genome.

(18) The sequence of each cosmid clone is determined. These sequences are then assembled into the sequence of the genome.

(4) Example C: Determining Sequences of a Genome Using cDNAs

The sequence of a genome provides much information about the long-term inherited DNA stored in the nucleus and about the genes on a genome. However, it is also useful to know how these genes are expressed and actually used in the cell. Toward this end, cDNA libraries have been constructed to assess gene expression in particular tissues, and methods such as direct selection have been developed to map these cDNAs relative to a genome (M. Lovett, J. Kere, and L. M. Hinton, "Direct selection: a method for the isolation of cDNAs encoded by large genomic regions," *Proc. Natl. Acad. Sci. U.S.A.*, vol. 88, pp. 9628–9632, 1991), incorporated by reference. Other methods such as exon trapping are similarly used to measure gene expression and map exons (A. J. Buckler, D. D. Chang, S. L. Graw, J. D. Brook, D. A. Haber, P. A. Sharp, and D. E. Housman, "Exon amplification: A strategy to isolate mammalian genes based on RNA splicing," *Proc. Natl. Acad. Sci. USA*, vol. 88, pp. 4005–4009, 1991), incorporated by reference. However, the current art provides no mechanism for high-throughput mapping of expressed gene sequences or their exons.

Referring to FIG. 1, an example method is described for determining sequences of a genome using cDNAs that is comprised of the steps:

(1) The cDNA library is obtained from a commercial vendor, or is constructed by RT-PCR from expressed mRNA and cloning into a bacteriophage lambda vector (F. M. Ausubel, R. Brent, R. E. Kingston, D. D. Moore, J. G. Seidman, J. A. Smith, and K. Struhl, ed., *Current Protocols in Molecular Biology*. New York, N.Y.: John Wiley and Sons, 1995; J. Sambrook, E. F. Fritsch, and T. Maniatis, Molecular Cloning, Second Edition. Plainview, N.Y.: Cold Spring Harbor Press, 1989), incorporated by reference.

(2) The individual lambda clones in the cDNA library are replicated, and then gridded onto nylon membranes.

(3) A WG-RH library is obtained (Research Genetics, Huntsville, Ala.) or constructed.

(4) DNA from each WG-RH is prepared using a method that preserves long stretches of species-specific genomic DNA. This can be done using long Alu-PCR on different restriction digests, and pooling the results. Alternatively, rather than Alu-Alu or Alu-linker (e.g., IRE-bubble) PCR, a linker-linker PCR can be performed, as described: genomic digestion, linker-fragment-linker ligation, Alu sequence selection, and PCR amplification. This preparation helps ameliorate inter-Alu PCR competition, and the species-specific selection is performed by a positive hybridization probe specific for species-specific (e.g., Alu in humans) repetitive DNA. An additional negative selection against the rodent (or other) background species can be done. Labeling proceeds by random priming.

(5) DNA comparison experiments are performed by serially hybridizing the labeled RH probes against the gridded cDNA library. The membranes are imaged, scored, and recorded.

(6) The cDNA clone library is then characterized by the long-range RH probes.

(7) STSs are used as bin probes for the RHs.

(8) PCR experiments probe the RHs with STSs.

(9) A table B comparing the RHs relative to the ordered STSs is produced or retrieved.

(10) IPM combines the CDNA vs. RH comparisons from step 6, together with the RH vs. STS comparisons from step 9. Initial IPM binning is done using the arithmetic inner product operation. These localizations are then optionally refined using a Markov chain Monte Carlo Bayesian analysis.

(11) An accurate binning of the CDNA library is produced.

(12) A short-range probe library is constructed relative to the cDNA clone library. These probes are very short-range (<1 Mb average fragment size) and highly multiplexed with great genomic complexity.

This construction is done by first digesting the genome's DNA sequence with an infrequent cutter of n bp (e.g., $n \leq 6$, such as Not1) restriction enzyme. Then, linkers suitable for PCR amplification are ligated onto both ends of the fragments. A collection of short DNA oligonucleotides is then constructed, so that at least one of these oligonucleotides occurs with probability p in a genome fragment; p is selected so that $0.05 \leq p < 0.95$. For example, with n=8, the average fragment size is $4^8$ bp, or ~64 kb. A random 9-mer occurs every $4^9$ bp, or ~256 kb; with a collection of two random 9-mers, one of the two 9-mers occurs roughly every ~128 kb. Therefore, $p \approx 0.50$, which leads to retention of roughly half of the fragments, forming a highly informative probe. By using several different restriction enzymes to construct the fragments, and, more essentially, many different random oligonucleotide collections to retain various informative fractions of the fragments, a very short-range probe library of 25–200 probes can be constructed.

Each probe is constructed by cutting the genome DNA with a selected restriction enzyme, ligating PCR linkers, and then selecting an informative subset by subtractive hybridization via a collection of end-biotinylated oligonucleotides linked to streptavidin coated magnetic beads (Dynal, Lake Success, N.Y.). PCR amplification is then performed. The PCR products are filled-in (polymerase), and then concatenated (kinase/ligase). Labeling is done via the random primer method.

In an alternative embodiment, a set of very high energy (i.e., $\leq 1$ Mb fragment size) RHs (David Cox, Stanford, Calif.) are used as a short-range probe library. These probes are expressed as previously described: genomic digestion, linker-fragment-linker ligation, Alu sequence selection, and PCR amplification. The selection and amplification are possibly repeated, and then followed by a labeling procedure.

(13) Serial hybridizations of the short-range probes are performed against the gridded cDNAs on membranes. This is done by hybridization, imaging, scoring, and recording the results.

(14) The result is a set of cDNAs (or exon fragments) that have been characterized by short-range probe fragments which are long relative to the cDNAs, but short relative to genome regions containing multiple cDNAs. Therefore the cDNAS can be ordered relative to the short-range probes using data analysis methods akin to RH-mapping, since the binning assumptions are similar.

(15) A BIN-SORT p rocedure is used to combine the long-range RH binning of the clone library from step 11, together with the very short-range probing of the clone library from step 14.

(16) The BIN-SORT produces a contig of the clone library which bins and orders cDNAs relative to the genome.

(17) A tiling path of cDNAS is formed that maps and spans gene regions.

(18) The sequences of these cDNA clones are determined using dideoxy sequencing methods, and the genes (and their exons) of the genome are thereby mapped and sequenced. Computer databases are then checked to infer the function of the gene.

(5) Example D: Determining the Sequence of a Genome Using Other Clones or Probes Example A described the method of FIG. 1 for large clones, example B for medium sized clones, and example C for small clones. For clone libraries whose inserts are between medium and large (e.g., PACs, BACs, P1s, etc), the protocol of example B is preferred.

For many applications, only two (instead of three) probings are required.

(1) For positional cloning applications, the detailed fine-grained contiging is often not required, so only the clone vs. long-range probe and long-range probe vs. bin probe comparisons need be performed (and the short-range probe vs. clone comparisons omitted). This is because the clones in the bins can be searched sequentially or in combination for the gene of interest.

(2) When using resolutions of RH probes that include very high energy (i.e., short fragment) RHs, the short-range probe vs. clone comparisons can similarly be omitted. This is because the high energy RHs themselves effectively serve as short-range probes.

(3) When the noise in the clone vs. long-range probe comparison experiments is reduced (e.g., by using IRE-bubble PCR probes), only the short-range probe vs. clone comparisons are needed (and the long-range probe vs. bin probe comparisons omitted). This is because the short-range probings can be used to "clean up" the low-noise clone vs. long-range probe hybridization data by using sets of mapped clones. The combined RH signature of a set of proximate clones can prove sufficiently clean for conventional noise intolerant RH mapping analysis methods to accurately bin proximate clone sets relative to the genome.

Just as single clones from a clone library can be used as a short-range probe, pools of clones can also be used as a short-range probe in the method of FIG. 1. Step 11 produces binning information on the clones. For step 12, a short-range probe library is constructed. Each short-range probe in this library is comprised of a first set of clones selected from the clone library according to the constraint that the clones are well separated. This constraint is satisfied by use of the global binning information provided from step 11; "well separated" is defined as a distance of at least three times the clonal insert size. The comparison step 13 then identifies a second set of clones, each of which is proximate to one clone in the first set. Each clone in the second set has been binned in step 11, so comparison of the bins of the clones in the second set with the bins of the clones in the first set then determines in step 14 a function that maps each clone in the second set to its unique clone in the first set. That is, the binning information from step 11 enables a multiplexed pooling experiment, and a subsequent demultiplexing analysis. The pools in the short-range library may be constructed randomly or combinatorially, and are subject to the bin separation constraints.

(6) Example E: Determining the Sequence of a Genome Using Two Clone Libraries

It would be useful to have a fine-grained clone map of a cosmid library for both sequencing and positional cloning purposes. It would additionally be useful to have a fine-grained expression map of cDNAs or exons for positional candidate cloning. Referring to FIG. 1, an example method is described for mutually achieving both results that is comprised of the steps:

(1) Two clone libraries are obtained: a cosmid library and a cDNA library.

(2) DNA is prepared from individual clones in these two clone library for comparison experiments, and gridded onto separate nylon membranes.

(3) WG-RHs are obtained, as described.

(4) Species-specific WG-RH DNA is prepared for the hybridization comparison experiments. For the cosmid library hybridizations, this is done using IRE-bubble PCR, as described. For the cDNA library hybridizations, this is done using a linker-linker ligation and repetitive element selection, as described.

(5) Labeled RH DNA is serially probed against the gridded cosmids and cDNAs.

(6) This RH probing provides a long-range characterization of both the cosmid and cDNA libraries.

(7) STSs are obtained for use as bin probes that are suitable for positioning the DNA sequences of the WG-RH library relative to the genome.

(8) Conventional STS probing of the RHs is done, and an RH map is constructed.

(9) Step 8 produces a table B of RHs whose DNA sequences have been characterized by the ordered STSs relative to the genome.

(10) The cosmid vs. RH, and cDNA vs. RH characterizations from step 6 are combined with the RH vs. STS binning characterization from step 9 using an inner product operation.

(11) Step 10 produces a global binning of the cosmid library and of the cDNA library.

(12) One or more short-range probe libraries are constructed.

(12a) In the first preferred embodiment, a first short-range probe library is constructed as a set of 25–200 oligonucleotides of small length (5 bp–15 bp). Preferably, the library is comprised of 50–100 8-mers, and 50–100 9-mers that have been properly designed. These oligonucleotide sequences are designed to preferentially detect sequences in coding or control regions of genes, rather than repetitive elements in the genome.

(12b) In the second preferred embodiment, a second very short-range, highly multiplexed probe library is additionally constructed that has great genomic complexity, as described in step 12 of example C. In the construction of this probe library, each oligonucleotide collection that is used to retain informative fragment subsets is comprised of one oligonucleotide. These oligonucleotides are preferably in one-to-one correspondence with the oligonucleotides in the first short-range oligonucleotide probe library.

(13) Short-range probings are performed.

(13a) In the first preferred embodiment, the cosmid and cDNA libraries are both probed with the first short-range probe library.

(13b) In the second preferred embodiment, the cosmid library is probed with the first short-range probe library, and the CDNA library is probed with the second short-range probe library.

(14) The cosmid and CDNA libraries are then each characterized by at least one short-range probe library.

(15) The RH binning of the cosmid library from step 11 is combined together with the oligonucleotide hybridization probing of the cosmid library from step 14.

(16) Step 15 produces a contig of the cosmid library which bins and orders the cosmids relative to the genome.

(16n) This cosmid vs. oligonucleotide information additionally bins and partially orders the short-range oligonucleotide probe sequence information relative to the genome. This map of oligonucleotides in genome regions is useful as a framework for mapping the cDNAs. The 50–100 8-mers provide an approximately average 1 kb spacing of binned oligonucleotides, and the 50–100 9-mers provide an approximately average 4 kb spacing of binned oligonucleotides. With a 5x coverage of 40 kb cosmids, the oligonucleotide binning resolution is about 10 kb, whereas with a 10x coverage of 40 kb cosmids, the oligonucleotide binning resolution is about 5 kb.

(16a) In the first preferred embodiment, the oligonucleotide probings of the CDNA library in step 13a are combined with the oligonucleotide map from step 16n to map the cDNAs. This is done by a form of sequencing-by-hybridization (SBH) mapping on the cDNAs. A CDNA is expected to be hit by one or more oligonucleotide probes. Within a local area (provided by the IPM binning of the CDNA in step 11), one oligonucleotide match will often suffice to bin the cDNA sequence. With two or more oligonucleotide matches to a bin, the local oligonucleotide map from step 16n will place uniquely (with very high probability) the cDNA in the region, up to the 5–10 kb resolution of the oligonucleotide binning from the cosmid map. This generally suffices to map a gene. Additional 8-mer or 9-mer oligonucleotide probings can be done to ensure that with high probability two or more oligonucleotide matches are observed.

(16b) In the second preferred embodiment, the second complex short-range probe library comparisons with the CDNA library from step 13b are combined with oligonucleotide map of step 16n to map the cDNAs. Each oligonucleotide on the genome may retain a fragment that contains it, and thereby provide a small hybridization neighborhood (the size of the fragment) containing the oligonucleotide location on the genome. These oligonucleotide-fragment neighborhoods extend the probing power of a small oligonucleotide to a larger region. Each cDNA clone has been globally binned in step 11 to a small (e.g., ≦5 Mb) region on the genome. For each cDNA clone, the second short-range library probings disclose a subset of oligonucleotide-fragment neighborhoods that intersect with the location and sequence of the cDNA. The intersection of these observed probe neighborhoods (indexed by oligonucleotide) is compared with the oligonucleotide bins on the local map of step 16n. When there is considerable consensus at a bin, the CDNA is mapped to that bin.

(17) A tiling path of cosmids is formed that span genome regions. The cDNAs are mapped relative to this cosmid map.

(18) The sequences of the cosmids on the tiling path, and of the cDNAs, are determined. This provides the sequence of the entire genome, and annotates it with expressed sequence information.

An aspect of this method is the construction of a framework map of closely spaced oligonucleotide sequence bins using the cosmid clones. Although the oligonucleotide probings of a cDNA may not be perfectly clean, the information suffices in a small (globally binned) genome region to locally bin the cDNA at very high resolution. This is analogous to how, on a larger scale, a radiation hybrid map constructs a framework map of binary signature bins using RHs. Although the RH probings of a clone may not be perfectly clean, the information suffices for IPM to globally bin the clone at high resolution.

(7) Utility of the Sequence of a Genome
Application: Gene Finding

An integrated clone map is constructed by the method of FIG. 1. When the bin probes include polymorphic genetic markers, and these markers are typed against the DNAs of member of families carrying a genetic trait, that trait can be genetically localized on the map relative to one or more bin probes. Depending on the study design, this genetic localization can be carried out using one of a variety of methods (G. M. Lathrop and J.-M. Lalcuel, "Efficient computations in multilocus linkage analysis," *Amer. J. Hum. Genet.*, vol. 42, pp. 498–505, 1988; T. C. Matise, M. W. Perlin, and A. Chakravarti, "Automated construction of genetic linkage maps using an expert system (MultiMap): application to 1268 human microsatellite markers," *Nature Genetics*, vol. 6, No. 4, pp. 384–390, 1994; E. S. Lander and D. Botstein, "Mapping Complex Genetic Traits in Humans: New Methods Using a Complete RFLP Linkage Map," in *Cold Spring Harbor Symposia on Quantitative Biology*, vol. LI, Cold Spring Harbor, Cold Spring Harbor Laboratory, 1986, pp. 49–62; L. Penrose, *Ann. Eugenics*, vol. 18, pp. 120–124, 1953; N. E. Morton, *Am. J. Hum. Genet.*, vol. 35, pp. 201–213, 1983; N. Risch, *Am. J. Hum. Genet.*, vol. 40, pp. 1–14, 1987; E. Lander and D. Botstein, *Genetics*, vol. 121, pp. 185–199, 1989; N. Risch, "Linkage strategies for genetically complex traits," in three parts, *Am. J. Hum. Genet.*, vol. 46, pp. 222–253, 1990; N. Risch, *Genet. Epidemiol.*, vol. 7, pp. 3–16, 1990; N. Risch, *Am. J. Hum. Genet.*, vol. 48, pp. 1058–1064, 1991; P. Holmans, "Asymptotic Properties of Affected-Sib-Pair Linkage Analysis," *Am. J. Hum. Genet.*, vol. 52, pp. 362–374, 1993; N. Risch, S. Ghosh, and J. A. Todd, "Statistical Evaluation of Multiple-Locus Linkage Data in Experimental Species and Its Relevance to Human Studies: Application to Nonobese Diabetic (NOD) Mouse and Human Insulin-dependent Diabetes Mellitus (IDDM)," *Am. J. Hum. Genet.*, vol. 53, pp. 702–714, 1993; R. C. Elston, in *Genetic Approaches to Mental Disorders*, E. S. Gershon and C. R. Cloninger, ed. Washington D.C.: American Psychiatric Press, 1994, pp. 3–21), incorporated by reference.

Following genetic localization relative to the bin probes, the integrated contiged clone map provides an immediate means to proceed with positional cloning procedures. (D. Cohen, I. Chumakov, and J. Weissenbach, *Nature*, vol. 366, pp. 698–701, 1993; B.-S. Kerem, J. M. Rommens, J. A. Buchanan, D. Markiewicz, T. K. Cox, A. Chakravarti, M. Buchwald, and L.-C. Tsui, "Identification of the cystic fibrosis gene: genetic analysis," *Science*, vol. 245, pp. 1073–1080, 1989; J. R. Riordan, J. M. Rommens, B.-S. Kerem, N. Alon, R. Rozmahel, z. Grzelczak, J. Zielenski, S. Lok, N. Plavsic, J.-L. Chou, M. L. Drumm, M. C. Iannuzzi, F. S. Collins, and L.-C. Tsui, "Identification of the cystic fibrosis gene: cloning and characterization of complementary DNA," *Science*, vol. 245, pp. 1066–1073, 1989), incorporated by reference. When an expression of candidate genes is included in the mapping resource (e.g., ESTs, cDNAs), the search may proceed more rapidly. When the genome sequences of the clones in the region have been determined, the gene search may be done in part using computer searches for candidate genes.

Application: Structure/Function Relation

The sequence of a genome is determined by the method of FIG. 1. From this genome sequence, the relation of a gene or its promoters to other known functions may be determined using similarity or homology searches. Protocols for these determinations are well described (N. J. Dracopoli, J. L. Haines, B. R. Korf, C. C. Morton, C. E. Seidman, J. G. Seidman, D. T. Moir, and D. Smith, ed., *Current Protocols in Human Genetics*. New York: John Wiley and Sons, 1995), incorporated by reference. The use of expressed sequence tag (EST) databases (Merck Gene Index, St. Louis, Mo.; Human Genome Sciences, Gathersburg, Md.) together with the genome sequence provides a highly effective means for rapidly correlating a gene's sequence with the structure and function of its protein products.

Application: Metabolic Network Determination

The sequence of a genome is determined by the method of FIG. 1. Using the RT-PCR technique of differential display, perturbations on the cell state can be assayed in terms of DNA expression. Select perturbations can elucidate the metabolic networks of coupled enzyme systems in the cell. Reference back to the DNA sequence of the genome provides information about local control and gene/promoter interactions. This information can be used to understand disease mechanisms and to develop new pharmaceutical agenst to alleviate said diseases.

Application: Growth and Development

The sequence of a genome is determined by the method of FIG. 1. Combining example B and example C, a method is described for constructing an integrated genetic-physical-expression map that includes the genome sequence and cDNAs. It is currently impractical to map very large numbers of cDNAs at high resolution, due to the currently used technology of sequencing each cDNA, constructing PCR primers for it, and then performing multiple PCR amplifications and detections relative to a panel of RHs to accurately map even a single cDNA. However unobvious it may currently seem to those skilled in the art, it would nonetheless be extremely desirable for elucidating the mechanism of cell growth and organism development to construct and map tissue-specific cDNA expression libraries at numerous points (e.g., at least every 24 hours) early in organism development. Further, the mapping of these expressed sequences back to their genomic locations would provide information on candidate genes, local gene expression, the coordination of normal and diseased cellular function under genetic control, and the time course of development in different tissues that would be highly useful in developing new diagnostic tests and therapeutic treatments for human disease. The method of the said examples provides such a novel means for practical rapid and high-resolution mapping of many expression libraries that would otherwise be neither constructed nor mapped.

Application: Drug Development

A sequence and map of a genome is determined by the method of FIG. 1. The sequence of the human genome or integrated clone maps can be used to identify genes that are causative for human disease. From such genes, and their DNA promoters and protein products, mechanisms of diseases related to said genes can be determined. Pharmacological agents that intervene at key junctures in gene-related functions can then be devised to specifically circumvent and treat diseases related to these genes.

Application: Diagnostic Testing

A sequence and map of a genome is determined by the method of FIG. 1. The sequence of the human genome or integrated clone maps can be used to identify genes that are causative for human disease. From such genes, and their DNA promoters and protein products, mechanisms of diseases related to said genes can be determined. Diagnostic tests that detect key junctures in gene-related structures and functions can then be devised to diagnose diseases related to these genes, and develop kits.

Application: Animal Models

The sequence of a genome is determined by the method of FIG. 1. In the current art, sequencing even one complete mammalian genome is a highly debated and very expensive proposition (estimated to cost around one billion dollars) which is not likely to be performed more than once. However, the novel sequencing method described renders sequencing more practical, since it produces a high-resolution clone map which can be used to cost-effectively direct the sequencing effort and to practically assemble the resulting sequences. Given the pressing medical need for sequencing a mammalian genome, and the absence of any such useful coordinating map, clearly the described invention is highly nonobvious.

By constructing a map as described in the method of FIG. 1, the upfront burden of building maps for mammalian species other than humans is considerably reduced. Further, since the cost per base of sequencing is expected to diminish, particularly as newer sequencing technologies become established, the described method provides the first useful starting point for beginning (and eventually completing) the DNA sequence determination of model animal genomes. Comparison of the DNA sequences and genes between human and model organisms is a well-established route for understanding and treating human disease.

Application: Somatic Cell Hybrids

Step 10 of the method of FIG. 1 describes an inner product mapping analysis mechanism. Referring to FIG. 3, localization profiles are produced that can localize DNA sequences to high resolution. This inner product operation can be applied to somatic cell hybrid deletion panel data, thereby increasing the utility of such data by providing more confident and higher resolution localizations.

Application: Genome Mismatch Scanning

Genome mismatch scanning (GMS) (S. F. Nelson, J. H. McCusker, M. A. Sander, Y. Kee, P. Modrich, and P. O. Brown, "Genomic mismatch scanning: a new approach to genetic linkage mapping," *Nature Genetics*, vol. 4, No. May, pp. 11–18, 1993), incorporated by reference, has been described as powerful hybridization-based approach to genetic linkage mapping. GMS has applications both in the mapping of genetic traits and in the diagnosis and prevention of disease. What is currently impeding practical application of the GMS method is the lack of a sequence or map of the human (or animal model) genome that would provide densely spaced (e.g., $\leq 1Mb$) hybridization probes for the genome sampling step that scans the mismatched genome DNAs. Applicant's invention discloses a practical method for constructing such a sequence or map of a genome using the method of FIG. 1 in the specification. In a preferred embodiment, densely spaced subsequences from the constructed sequence of a genome are used as hybridizatio probes in GMS. In an alternative embodiment, densely spaced clones (or subsequences therefrom) from the constructed map of a genome are used as hybridizatio probes in GMS.

Application: Reliable Maps from Unreliable Data

A sequence and map of a genome is determined by the method of FIG. 1. It is generally believed that such maps can be reliably constructed only from highly reliable and relatively complete data. This belief adds considerably to the time, expense, and effort currently expended in constructing genome maps. However, the method of FIG. 1 discloses a novel mechanism for constructing highly reliable maps from unreliable and incomplete data (J. von Neumann, "Probabilistic logics and the synthesis of reliable organisms from unreliable components," in *Automata Studies*, C. E. Shannon and J. McCarthy, ed. Princeton, N.J.: Princeton University Press, 1956, pp. 43–98), incorporated by reference. Specifically:

In step 6, table A's long-range characterization of the clone library can be comprised of very noisy, highly unreliable hybridization data exhibiting large error rates.

In step 9, table B's characterization of the long-range probe library can be sparsely sampled. In some embodiments, a $\leq 1$ Mb average inter-bin distance suffices for accurate mapping and contig construction.

In step 14, table D's short-range characterization of the clone library has a high tolerance for data errors.

This unobvious result is due to the considerable redundancy in the three data tables, and to the noise filtering and consistency cross-checking capabilities of the analysis methods:

In step 11, table C is a highly reliable binning because the clean PCR-based data table B is used as a global corrective for the noisy complex hybridization-based data table A. This has been empirically demonstrated for human chromosome 11.

In step 16, table E is a highly reliable contiging because every clone has been probed with both long-range and short-range data. Therefore, the global binning information relaxes the requirements on the short-range probings: useful comparisons can be made within a relatively small bin region using imperfect data.

Thus, the described invention produces a novel, useful, and unobvious synergy between distinct data sets that enables the practical construction of highly reliable clone maps and DNA sequences from imperfect data. Note that this imperfect data allows orders of magnitude reductions in the time, expense, and effort of experimental comparisons relative to the current art. For example, the chromosome 11 inner product map of RPCI YACs was constructed (data generation and analysis) in under six months, for under $20,000, and required only 241 hybridization experiments.

Herein, means or mechanism for language has been used. The presence of means is pursuant to 35 U.S.C. §112 paragraph and is subject thereto. The presence of mechanism is outside of 35 U.S.C. §112 and is not subject thereto.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method of mapping a region of a genome comprised of the steps:
   (a) obtaining nucleic acid material from a genome;
   (b) constructing a clone library and a long-range probe library from said nucleic acid material;
   (c) hybridizing labeled long-range probes to the clone library to form pairing between homologous nucleic acid sequences;
   (d) detecting the labels of the long-range probes paired with the clone library to form signals;
   (e) recording the signals to form a set of data; and
   (f) combining said set of data with calibration information in a computing device with memory to construct a map of the clones which covers the region of the genome.

2. The method of claim 1, wherein said clone library has an average DNA insert size not exceeding 350 kilobases.

3. The method of claim 1, wherein said clone library includes bacterial or phage cloning vectors.

4. The method of claim 1, wherein said clone library has a number of clones at least twice the total genome length divided by the average clone insert size.

5. The method of claim 1, wherein said genome is a mammalian genome.

6. The method of claim 5, wherein said mammalian genome is a human genome.

7. The method of claim 1, wherein the long-range probe library consists of chromosomal DNA from somatic cell hybrids.

8. The method of claim 1, wherein the long-range probe library consists of genome fragments in radiation hybrid form.

9. The method of claim 1, wherein the set of data does not accurately correspond to chromosomal colocalization of probe and clone DNA sequences.

10. The method of claim 1, wherein step c includes hybridizing to at least 73 long-range probes.

11. A method for identifying and isolating a gene linked to a genetic trait comprised of the steps:
    (a) constructing a clone map of a region of a genome according to the method of claim 1; and
    (b) deriving DNA sequences from the clones in said map to aid in positional cloning and thereby identifying and isolating a gene linked to a genetic trait.

12. The method of claim 11, wherein said gene is related to a human disease.

13. A method of forming a tiling path of overlapping clones comprising the steps of:
    (a) obtaining nucleic acid material from a genome;
    (b) constructing a clone library and a long-range probe library from said nucleic acid material;
    (c) hybridizing labeled long-range probes to the clone library to form pairing between homologous nucleic acid sequences;
    (d) detecting the labels of the long-range probes paired with the clone library to form signals;
    (e) recording the signals to form a first set of data;
    (f) performing short-range probings on the clone library with probes from a short-range probe library to form a second set of data different from the first set of data;
    (g) combining said first set of data and said second set of data to construct a map of the clones relative to said genome; and
    (h) producing sets of mapped overlapping clones from the clones in the clone library, thereby forming a tiling path of mapped overlapping clones.

14. The method of claim 13, wherein the short-range probe library consists of oligonucleotides of size between 5 base pairs and 15 base pairs.

15. The method of claim 13, wherein the short-range probe library consists of a plurality of clones.

16. A method of sequencing a genome comprising the steps of:
    (a) constructing a tiling path of overlapping clones according to the method of claim 13;
    (b) determining the DNA sequences of the clones in the tiling path; and
    (c) combining these DNA sequences to form mapped DNA sequences, thereby sequencing said genome.

17. A method of mapping an expressed gene relative to a genome comprising the steps of:
    (a) obtaining an expressed gene whose corresponding gene is present in said genome;
    (b) labeling said expressed gene;
    (c) hybridizing the labeled expressed gene with clones in the tiling path constructed according to the method of claim 13, to form detections;
    (d) recording said detections to form a third set of data, different from the first and second sets of data from claim 13; and
    (e) combining said third set of data with the genome locations of the clones in the tiling path to map the expressed gene relative to said genome.

18. A method of performing a genetic linkage mapping comprising the steps of:
    (a) constructing a tiling path of overlapping clones according to the method of claim 13; and
    (b) using clones in the tiling path as hybridization probes in a genetic linkage mapping.

19. The method of claim 18 wherein the genetic linkage mapping is a genome mismatch scanning.

* * * * *